United States Patent
Casavant et al.

(10) Patent No.: US 10,864,378 B2
(45) Date of Patent: Dec. 15, 2020

(54) PACEMAKER WITH DIAGNOSTIC INTRINSIC BEAT SEARCH

(71) Applicant: CARDIAC PACEMAKERS, INC., St. Paul, MN (US)

(72) Inventors: David A. Casavant, Reading, MA (US); Jeffrey E. Stahmann, Ramsey, MN (US); Carolina Villarreal, Hopedale, MA (US); James O. Gilkerson, Stillwater, MN (US); Deepa Mahajan, Roseville, MN (US); Paul Richard Holleran, Grafton, MA (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 300 days.

(21) Appl. No.: 15/915,700

(22) Filed: Mar. 8, 2018

(65) Prior Publication Data
US 2018/0256908 A1   Sep. 13, 2018

Related U.S. Application Data

(60) Provisional application No. 62/469,257, filed on Mar. 9, 2017.

(51) Int. Cl.
*A61N 1/372*   (2006.01)
*A61N 1/375*   (2006.01)
(Continued)

(52) U.S. Cl.
CPC ....... *A61N 1/37282* (2013.01); *A61N 1/3622* (2013.01); *A61N 1/36507* (2013.01);
(Continued)

(58) Field of Classification Search
CPC .. A61N 1/3622; A61N 1/365; A61N 1/36542; A61N 1/3627
(Continued)

(56) References Cited

U.S. PATENT DOCUMENTS

| 4,263,915 A | 4/1981 | McDonald et al. |
| 4,363,325 A | 12/1982 | Roline et al. |

(Continued)

FOREIGN PATENT DOCUMENTS

WO   2006096100 A1   9/2006

OTHER PUBLICATIONS

The Danish Multicenter Randomised Study on AAI Versus DDD Pacing in Sick Sinus Syndrome—Study First Received Oct. 10, 2005; Last Updated Feb. 20, 2009. http://clinicaltrials.gov, 4 pages.

(Continued)

*Primary Examiner* — Carl H Layno
*Assistant Examiner* — Jon Eric C Morales
(74) *Attorney, Agent, or Firm* — Seager. Tufte & Wickhem LLP.

(57) ABSTRACT

Regulating cardiac activity may include pacing the patient's heart at a starting pacing rate and instigating an intrinsic heart beat search algorithm that includes pacing at a reduced rate for a period of time and capturing electrical signals representative of cardiac electrical activity while pacing at the reduced rate in order to determine a presence or absence of intrinsic heart beats. If intrinsic heart beats are not detected, the heart may be paced at a further reduced rate for a period of time. If intrinsic beats are detected, the heart may be paced again at the starting pacing rate. This may continue until intrinsic heart beats are detected or until a lower search rate limit is reached. Diagnostic data may be collected at each stage and transmitted to a display device for analysis by a physician or the like.

19 Claims, 19 Drawing Sheets

(51) Int. Cl.
   *A61N 1/39*      (2006.01)
   *A61N 1/362*     (2006.01)
   *A61N 1/37*      (2006.01)
   *A61N 1/365*     (2006.01)
   *A61N 1/378*     (2006.01)

(52) U.S. Cl.
   CPC ..... *A61N 1/36535* (2013.01); *A61N 1/36542* (2013.01); *A61N 1/36564* (2013.01); *A61N 1/36578* (2013.01); *A61N 1/36592* (2013.01); *A61N 1/3712* (2013.01); *A61N 1/3756* (2013.01); *A61N 1/3787* (2013.01); *A61N 1/37217* (2013.01); *A61N 1/3956* (2013.01)

(58) Field of Classification Search
   USPC ..................................................... 607/9, 14
   See application file for complete search history.

(56) References Cited

U.S. PATENT DOCUMENTS

| | | | |
|---|---|---|---|
| 4,554,920 A | 11/1985 | Baker et al. | |
| 4,554,921 A | 11/1985 | Boute et al. | |
| 4,856,523 A | 8/1989 | Sholder et al. | |
| 5,247,929 A | 9/1993 | Stoop et al. | |
| 5,247,930 A | 9/1993 | Begemann et al. | |
| 5,284,491 A | 2/1994 | Sutton et al. | |
| 5,522,858 A | 6/1996 | Van der Veen | |
| 5,534,017 A | 7/1996 | Van Krieken et al. | |
| 5,683,426 A | 11/1997 | Greenhut et al. | |
| 6,389,316 B1 | 5/2002 | Bomzin et al. | |
| 6,408,210 B1 | 6/2002 | Bomzin et al. | |
| 6,424,865 B1 | 7/2002 | Ding | |
| 6,434,428 B1 | 8/2002 | Sloman et al. | |
| 6,493,583 B1 | 12/2002 | Levine et al. | |
| 6,748,270 B2 | 6/2004 | Rouw et al. | |
| 6,978,177 B1* | 12/2005 | Chen | A61N 1/3622 607/14 |
| 7,532,930 B2 | 5/2009 | Schermeier et al. | |
| 8,019,417 B2 | 9/2011 | Bomzin et al. | |
| 8,892,197 B2 | 11/2014 | Ujhelyi et al. | |
| 9,119,547 B2 | 9/2015 | Cazares et al. | |
| 9,375,579 B2 | 6/2016 | Casavant et al. | |
| 9,375,580 B2 | 6/2016 | Bonner et al. | |
| 9,393,424 B2 | 7/2016 | Demmer et al. | |
| 9,399,139 B2 | 7/2016 | Demmer et al. | |
| 2002/0161409 A1 | 10/2002 | Rouw et al. | |
| 2005/0149138 A1 | 7/2005 | Min et al. | |
| 2006/0064027 A1 | 3/2006 | Borowitz et al. | |
| 2006/0224197 A1 | 10/2006 | Havel et al. | |
| 2008/0004664 A1* | 1/2008 | Hopper | A61N 1/3627 607/9 |
| 2012/0259234 A1 | 10/2012 | Lindgren | |
| 2016/0114161 A1 | 4/2016 | Amblard et al. | |
| 2016/0310733 A1 | 10/2016 | Sheldon et al. | |

OTHER PUBLICATIONS

International Search Report—PCT/EP2009/067787, filed Dec. 22, 2009.

Written Opinion—PCT/EP2009/067787, filed Dec. 22, 2009.

\* cited by examiner

PACEMAKER WITH DIAGNOSTIC INTRINSIC BEAT SEARCH

CROSS REFERENCE TO RELATED APPLICATIONS

This application claims the benefit of U.S. Provisional Patent Application Ser. No. 62/469,257 filed on Mar. 9, 2017, the disclosure of which is incorporated herein by reference.

TECHNICAL FIELD

The present disclosure pertains to medical devices, and more particularly to medical devices such as pacemakers that sense cardiac activity of a patient's heart and deliver therapy to the patient's heart.

BACKGROUND

Implantable medical devices are commonly used today to monitor physiological or other parameters of a patient and/or deliver therapy to a patient. For example, to help patients with heart related conditions, various medical devices (e.g., pacemakers, defibrillators, etc.) can be implanted in a patient's body. Such devices may monitor and in some cases provide electrical stimulation (e.g. pacing, defibrillation, etc.) to the heart to help the heart operate in a more normal, efficient and/or safe manner. In another example, neuro stimulators can be used to stimulate tissue of a patient to help alleviate pain and/or other condition. In yet another example, an implantable medical device may simply be an implantable monitor that monitors one or more physiological or other parameters of the patient, and communicates the sensed parameters to another device such as another implanted medical device or an external device.

In some cases, such as after a Transcatheter Aortic Valve Replacement (TAVR) procedure, the heart's conduction system is stunned or damaged to the extent that the patient may temporarily (and sometimes permanently) require ventricular pacing in order to maintain an adequate heart rhythm. In some percentage of cases, the conduction system will recover to the point where the heart can again sustain intrinsically conducted beats on its own. In other cases, the conduction system is permanently damaged. It is often not known which of the patients will experience improvement in their conduction system and which will not.

SUMMARY

The present disclosure pertains to a medical device that is able to collect data from time to time regarding the heart's ability to produce intrinsic beats, and to report such data to a physician or the like for evaluation. In some cases, the medical device may be configured to change a therapy based on the collected data. It is contemplated that the medical device may be an implantable medical devices (IMD) such as but not limited to a leadless cardiac pacemaker (LCP), a subcutaneous implantable cardioverter defibrillator (SICD), a transvenous implantable cardioverter defibrillator, an implantable monitor (IM), and/or the like. In some cases, the medical device may deliver data to one or more external medical devices such as a device programmer and/or other external medical device.

In one example, an implantable medical device (IMD) is configured to sense electrical cardiac activity of a patient's heart and to pace a ventricle of the patient's heart. The illustrative IMD includes a housing and a plurality of electrodes. A controller is disposed within the housing and is operably coupled to the plurality of electrodes such that the controller can receive electrical signals from at least two of the plurality of electrodes representing electrical cardiac activity and can deliver pacing pulses to the ventricle of the patient's heart via at least two of the plurality of electrodes. A communications module may be operably coupled to the controller and may be configured to wirelessly communicate with a remotely located device. The controller may be configured to pace the ventricle of the patient's heart at a therapy based pacing rate using a plurality of pacing pulses, but where one or more of the plurality of pacing pulses may be inhibited by a corresponding sensed intrinsic beat. The controller may also be configured to perform an intrinsic beat search algorithm. During the intrinsic beat search algorithm, the controller may be configured to identify a first reduced pacing rate representing a reduction relative to the therapy based pacing rate, pace the ventricle of the patient's heart for a period of time at the first reduced pacing rate using a plurality of pacing pulses, but where one or more of the plurality of pacing pulses may be inhibited by a corresponding sensed intrinsic beat, and determine if there are sustained intrinsic beats at the first reduced pacing rate.

Alternatively or additionally, if there are sustained intrinsic beats at the first reduced pacing rate, the controller may be configured to return to pace the ventricle of the patient's heart at the therapy based pacing rate.

Alternatively or additionally, the controller may be configured to return to pace the ventricle of the patient's heart at the therapy based pacing rate in a single rate step.

Alternatively or additionally, the controller may be configured to return to pace the ventricle of the patient's heart at the therapy based pacing rate increasingly over time.

Alternatively or additionally, if there are not sustained intrinsic beats at the first reduced pacing rate, the controller may be configured to identify a second reduced pacing rate representing a reduction relative to the first reduced pacing rate, pace the ventricle of the patient's heart for a period of time at the second reduced pacing rate using a plurality of pacing pulses, but where one or more of the plurality of pacing pulses may be inhibited by a corresponding sensed intrinsic beat, and determine if there are sustained intrinsic beats at the second reduced pacing rate.

Alternatively or additionally, the controller may be configured to continue to reduce the pacing rate and capture electrical signals while pacing at a further reduced pacing rate in order to determine a presence or absence of intrinsic heart beats until intrinsic heart beats are detected or until a lower rate search limit is reached.

Alternatively or additionally, if there are sustained intrinsic beats at the second reduced pacing rate, the controller may be configured to return to pace the ventricle of the patient's heart at the therapy based pacing rate.

Alternatively or additionally, if there are not sustained intrinsic beats at the second reduced pacing rate, the controller may be configured to identify a third reduced pacing rate representing a reduction relative to the second reduced pacing rate, pace the ventricle of the patient's heart for a period of time at the third reduced pacing rate using a plurality of pacing pulses but where one or more of the plurality of pacing pulses may be inhibited by a corresponding sensed intrinsic beat, and determine if there are sustained intrinsic beats at the third reduced pacing rate.

Alternatively or additionally, if there are sustained intrinsic beats at the third reduced pacing rate, the controller may be configured to return to pace the ventricle of the patient's heart at the therapy based pacing rate.

Alternatively or additionally, the controller may be further configured to record one or more items at each reduced pacing rate, the one or more items including one or more of a beat type for each beat, wherein the beat type includes an intrinsic beat or a paced beat, a beat rate, wherein the beat rate represents the rate at which the beats occur, a beat rate variability, wherein the beat rate variability represents the rate variability at which the beats occur, and an egram.

Alternatively or additionally, the controller may be configured to record one or more items over time.

Alternatively or additionally, the controller may be configured to transmit one or more of the items via the communications module to the remotely located device.

Alternatively or additionally, the controller may be further configured to record one or more items at each reduced pacing rate, the one or more items including one or more of a beat type for each beat, wherein the beat type includes an intrinsic beat or a paced beat, a beat rate, wherein the beat rate represents the rate at which the beats occur, a beat rate variability parameter, wherein the beat rate variability parameter represents the rate variability at which the beats occur, an egram, a respiration rate parameter, a posture parameter, one or more heart sound parameters, one or more contractility parameters, a QRS width parameter, a PR interval parameter, a QRS to S1 interval parameter, a blood pressure parameter, an activity level parameter, an AV delay parameter, and a p-wave indicator.

Alternatively or additionally, the controller may determine that there are sustained intrinsic beats when at least 80 percent of the beats are intrinsic beats.

Alternatively or additionally, the controller may determine that there are sustained intrinsic beats when at least 90 percent of the beats are intrinsic beats.

Alternatively or additionally, the therapy based pacing rate may be a lower pacing rate limit of the IMD.

Alternatively or additionally, the therapy based pacing rate may be above a lower pacing rate limit of the IMD and may be based on a detected patient activity level.

Alternatively or additionally, the controller may be configured to perform the intrinsic beat search algorithm at each of two or more different therapy based pacing rates that are based on two or more different detected patient activity levels.

Alternatively or additionally, the controller may be further configured to record one or more items at each of the two or more different therapy based pacing rates, wherein the one or more items includes one or more of a beat type for each beat, wherein the beat type includes an intrinsic beat or a paced beat, a beat rate, wherein the beat rate represents the rate at which the beats occur, a beat rate variability, wherein the beat rate variability represents the rate variability at which the beats occur, and an egram.

Alternatively or additionally, the IMD may further include a battery having a battery capacity that is sufficient to power the IMD for 6 months or less when pacing at max pacing power at a rate of 60 beats/minute.

In another example, a method of performing an intrinsic heart beat search in an implantable medical device while delivering pacing therapy to a patient's heart includes identifying a reduced pacing rate representing a reduction relative to a therapy based pacing rate and pacing the ventricle of the patient's heart for a period of time at the reduced pacing rate using a plurality of pacing pulses but where one or more of the plurality of pacing pulses may be inhibited by a corresponding sensed intrinsic beat. One or more items may be recorded, the one or more items may include one or more of a beat type for each beat, wherein the beat type includes an intrinsic beat or a paced beat, a beat rate, wherein the beat rate represents the rate at which the beats occur, a beat rate variability, wherein the beat rate variability represents the rate variability at which the beats occur, and an egram. A determination is made as to whether there are sustained intrinsic beats at the reduced pacing rate. The pacing, recording and determining steps are repeated using different reduced pacing rates and in response to determining that there are sustained intrinsic beats, pacing the ventricle of the patient's heart at the therapy based pacing rate.

Alternatively or additionally, the method may further include transmitting one or more of the items to a remotely located device.

In another example, a method of regulating cardiac activity following a procedure that may temporarily impair a cardiac conduction system within a patient's heart includes pacing the patient's heart at a starting pacing rate and instigating an intrinsic heart beat search algorithm. The intrinsic heart beat search algorithm may include pacing at a reduced rate for a period of time and capturing electrical signals representative of cardiac electrical activity while pacing at the reduced rate in order to determine a presence or absence of intrinsic heart beats. The method may further include pacing at a further reduced rate for a period of time if intrinsic heart beats are not detected, and returning to pacing at the starting pacing rate if intrinsic beats are detected. The method may further include continuing to reduce the pacing rate and capturing electrical signals while pacing at the further reduced pacing rate in order to determine a presence or absence of intrinsic heart beats until intrinsic heart beats are detected or until a lower search rate limit is reached.

Alternatively or additionally, the method may further include reporting results of the intrinsic heart beat search algorithm to a remote device.

In another example, an implantable medical device (IMD) may be configured to sense cardiac activity of a patient's heart via electrical, mechanical, acoustic or other means, and to pace a ventricle of the patient's heart. The IMD may include a housing, a plurality of electrodes and one or more sensors. A controller may be disposed within the housing and may be operably coupled to the plurality of electrodes such that the controller can receive electrical signals from at least two of the plurality of electrodes representing electrical cardiac activity and can deliver pacing pulses to the ventricle of the patient's heart via at least two of the plurality of electrodes. A communications module may be operably coupled to the controller and may be configured to wirelessly communicate with a remotely located device. The IMD may be configured to detect atrial contractions and the controller may be configured to pace the ventricle of the patient's heart using an initial AV delay after each atrial contraction for a plurality of cardiac cycles, but where one or more of the ventricular pacing pulses may be inhibited by a corresponding sensed ventricular intrinsic beat. The controller may be further configured to perform an intrinsic beat search algorithm during which the controller is configured to identify a first AV delay that is longer than the initial AV delay, pace the ventricle of the patient's heart using the first AV delay after each atrial contraction for a plurality of cardiac cycles, but where one or more of the ventricular pacing pulses may be inhibited by a corresponding sensed ventricular intrinsic beat, and determine if there is atrioventricular conduction, as indicated by sustained intrinsic beats, using the first AV delay.

Alternatively or additionally, if there are sustained atrioventricular conduction at the first AV delay, the controller may be configured to return to pace the ventricle of the patient's heart using the initial AV delay.

Alternatively or additionally, if there is not sustained atrioventricular conduction using the first AV delay, the controller may be configured to identify a second AV delay that is longer than the first AV delay, pace the ventricle of the patient's heart using the second AV delay after each atrial contraction for a plurality of cardiac cycles, but where one or more of the ventricular pacing pulses may be inhibited by a corresponding sensed ventricular intrinsic beat, and determine if there is sustained atrioventricular conduction using the second AV delay.

Alternatively or additionally, if there is sustained atrioventricular conduction at the second AV delay, the controller may be configured to return to pace the ventricle of the patient's heart using the initial AV delay.

The above summary of some illustrative embodiments is not intended to describe each disclosed embodiment or every implementation of the present disclosure. The Figures, and Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
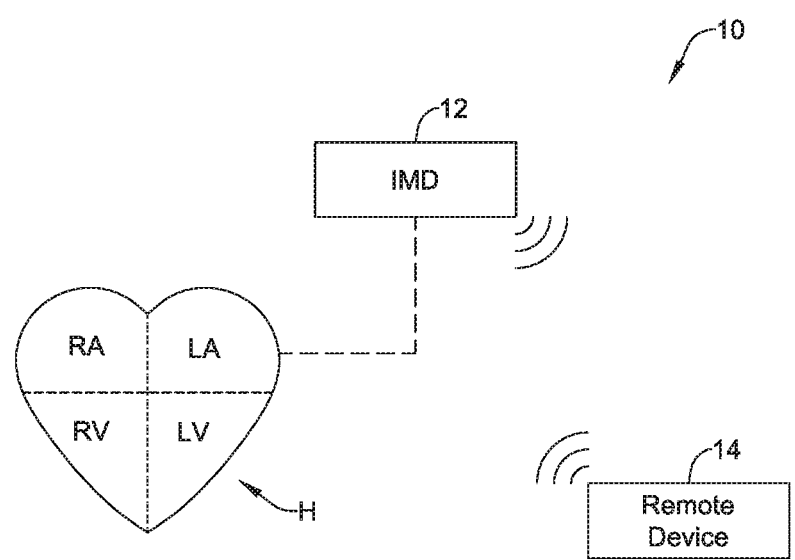
FIG. 1 is a schematic block diagram of a system including an implantable medical device (IMD) and a remote device in accordance with an example of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure. While the present disclosure is applicable to any suitable implantable medical device (IMD), the description below often uses pacemakers and more particularly leadless cardiac pacemakers (LCP) as particular examples.

FIG. 1 is a schematic diagram showing an illustrative system 10 that may be used to sense and/or pace a heart H. In some cases, the system 10 may also be configured to shock the heart H. The heart H includes a right atrium RA and a right ventricle RV. The heart H also includes a left atrium LA and a left ventricle LV. In some cases, the system 10 may include a medical device that provides anti-arrhythmic therapy to the heart H. In some cases, the system 10 may include an implantable medical device (IMD) 12 and a remote device 14. In some instances, the implantable medical device 12 may be implantable within the patient at a position near or even within the heart H. In some cases, the remote device 14 may be exterior to the patient. In some cases, the remote device 14 may be a programmer, for example, or other device that is configured to communicate with the IMD 12 and to display data received from the IMD 12. In some cases, there may be another IMD (not shown), that acts as an intermediary between the IMD 12 and the remote device 14.

Figure 2:
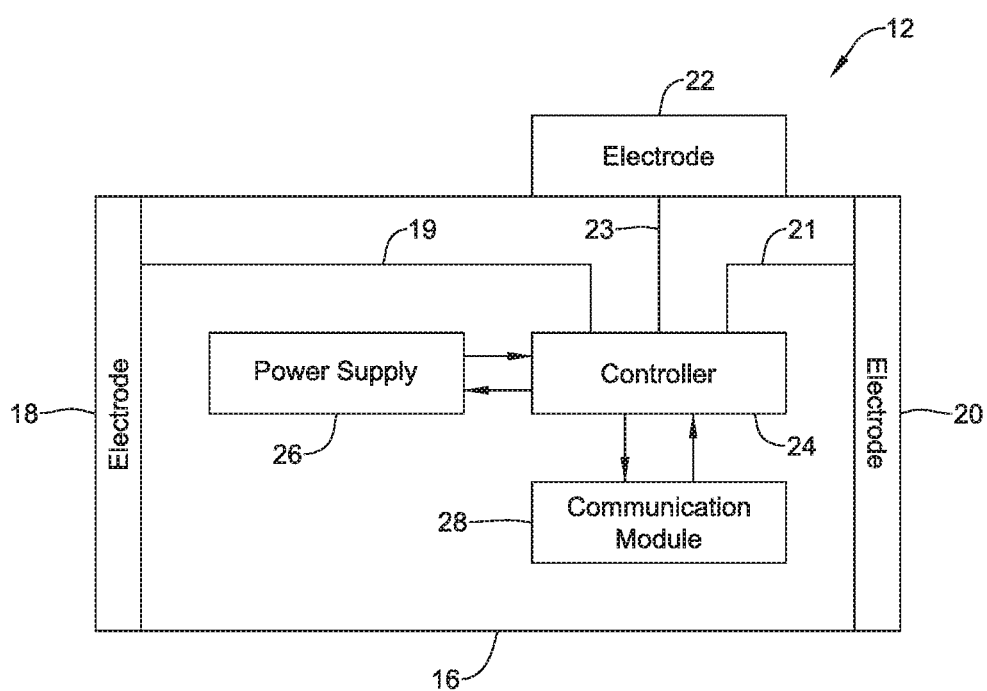
FIG. 2 is a schematic block diagram of the illustrative IMD of FIG. 1.
Figure 16:
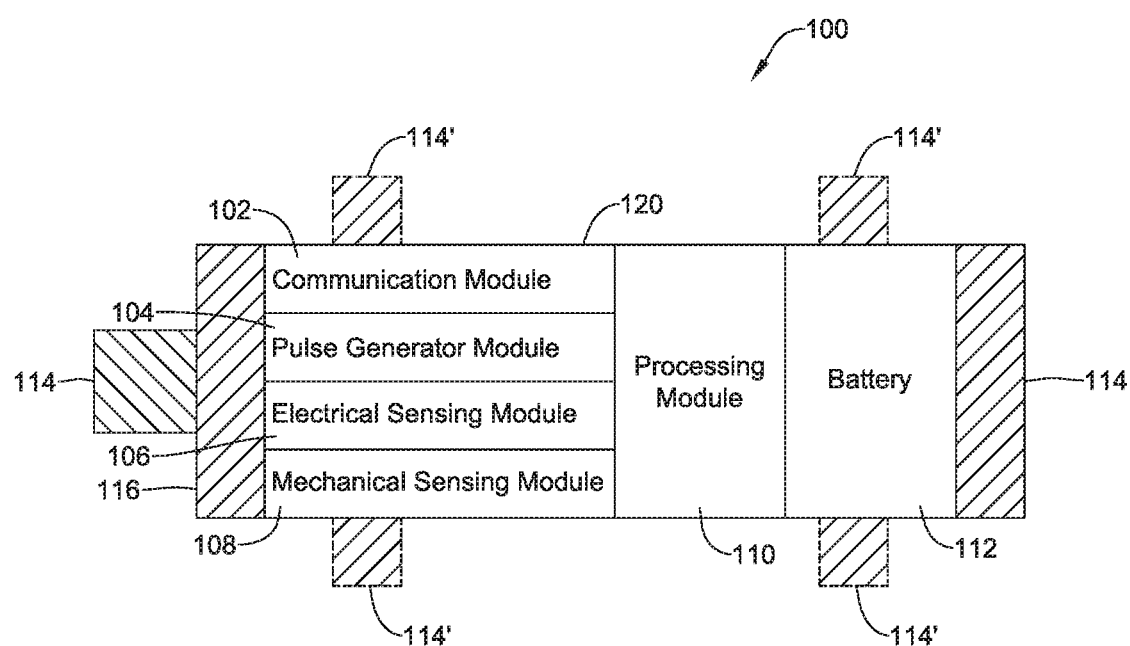
FIG. 16 is a more detailed schematic block diagram of an illustrative IMD in accordance with an example of the disclosure.
Figure 17:
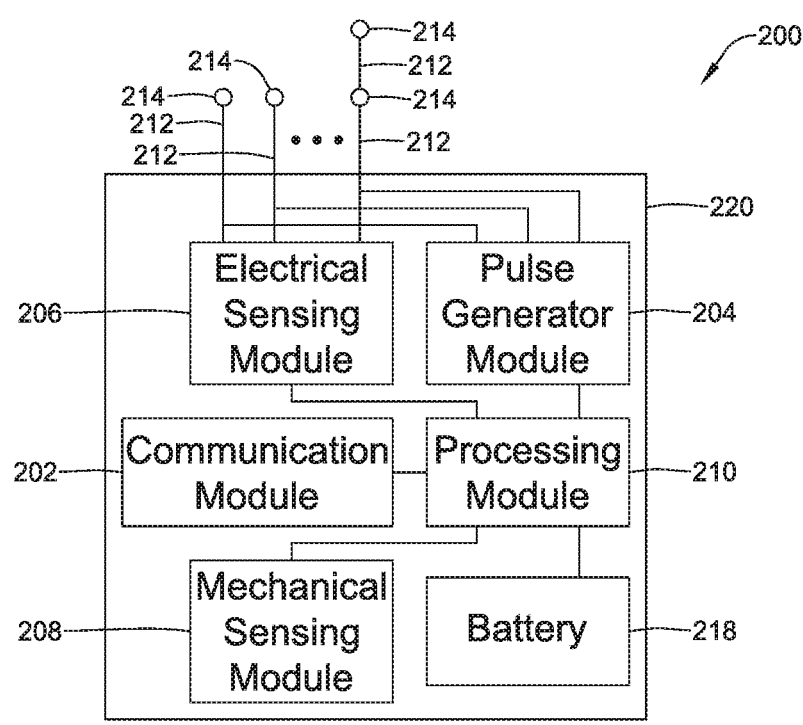
FIG. 17 is a schematic block diagram of another illustrative medical device that may be used in conjunction with the IMD of FIG. 16.

FIG. 2 is a schematic block diagram illustrating the IMD 12. In some cases, the IMD 12 may include a housing 16 and a plurality of electrodes that are disposed relative to the housing 16. In the example shown there is a first electrode 18, a second electrode 20 and a third electrode 22. In some cases, there may be only two electrodes. In some cases, the IMD 12 may include additional electrodes. In some cases, one or more of the electrodes 18, 20, 22 may be disposed on the housing 16. In some instances, the IMD 12 may be a leadless cardiac pacemaker (LCP), as schematically shown in FIG. 16. In some cases, one or more of the electrodes 18, 20, 22 may be disposed on an electrode support structure or lead, and thus may be separated from the housing 16. In some cases, the IMD 12 may be an implantable cardioverter defibrillator (ICD), such as a subcutaneous implantable cardioverter defibrillator (SICD), as shown in FIG. 17.

In the example shown, a controller 24 is disposed within the housing 16 and may be operably coupled to the electrodes 18, 20, 22 via electrical connectors 19, 21 and 23, respectively. A power supply 26 is operably coupled to the controller 24 and provides power for operation of the controller 24 as well as providing power for generating pacing pulses that can be delivered via at least two of the electrodes 18, 20, 22 via the controller 24. In some cases, the power supply 26 may be a battery. For a reduced sized or temporary IMD, the battery may have a battery capacity that is sufficient to power the IMD 12 for 6 months or less when pacing at max pacing power at a rate of 60 beats/minute. In other cases, the battery capacity may be sufficient to power the IMD for years.

In some cases, the controller 24 may be considered as being configured to generate and deliver a plurality of pacing pulses via a pair of the electrodes 18, 20, 22. In some cases, while not illustrated, the IMD 12 may include one or more other sensors such as an accelerometer or a gyro, for example (see FIGS. 16 and 17). In some cases, the controller 24 may be operably coupled to the electrodes 18, 20, 2 such that the controller 24 can receive electrical signals from at least two of the electrodes 18, 20, 22 representing electrical cardiac activity and can deliver pacing pulses to the ventricle of the heart H via at least two of the electrodes 18, 20, 22.

In some cases, the IMD 12 may include a communications module 28 that is operably coupled to the controller 24 and may be configured to receive messages from other devices, and in some cases send messages to other devices. In some instances, the communications module 28 may be configured to wirelessly communicate with a remotely located device such as the remote device 14 (FIG. 1). In some cases, the communications module 28 may enable the IMD 12 to receive messages from another implanted device. In some cases, the controller 24 may be configured to receive, via the communications module 28, messages communicated via conducted communication that may be picked up by the electrodes 18, 20, 22.

In some cases, as will be appreciated, the IMD 12 may be configured to sense electrical cardiac activity of the heart H and to pace the heart, such as the right ventricle RV or the left ventricle LV. In some cases, the controller 24 may be configured to pace the ventricle of the patient's heart H at a therapy based pacing rate using a plurality of pacing pulses, but where one or more of the plurality of pacing pulses may be inhibited by a corresponding sensed intrinsic beat.

The controller 24 may be configured to perform an intrinsic beat search algorithm. By performing an intrinsic beat search algorithm, which involves temporarily pacing at one or more reduced pacing rates, the controller 24 may be able to determine if the heart H is producing sustained intrinsic beats or not. If the heart H is producing sustained intrinsic beats, the IMD 12 may be able to pace less by lowering the therapy based pacing rate by an appropriate amount, and let the heart H beat in accordance with its intrinsic heart rate. The controller 24 may determine that there are sustained intrinsic beats at a reduced pacing rate if at least a predetermined percent of the beats are intrinsic beats. In some cases, the controller 24 may determine that there are sustained intrinsic beats at a reduced pacing rate if at least 80 percent of the beats are intrinsic beats. In some cases, the controller 24 may determine that there are sustained intrinsic beats if at least 90 percent of the beats are intrinsic beats. These are just examples.

During an illustrative intrinsic beat search algorithm, the controller 24 may be configured to identify a first reduced pacing rate representing a reduction relative to the therapy based pacing rate and to pace the ventricle of the patient's heart for a period of time at the first reduced pacing rate using a plurality of pacing pulses, but where one or more of the plurality of pacing pulses may be inhibited by a corresponding sensed intrinsic beat. The controller 24 may then determine if there are sustained intrinsic beats at the first reduced pacing rate. In some cases, if the controller 24 determines that there are sustained intrinsic beats at the first reduced pacing rate, the controller 24 may return to pace the ventricle of the patient's heart at the therapy based pacing rate. In some cases, when returning to the therapy based pacing rate, the controller 24 may return to pace the ventricle of the patient's heart at the therapy based pacing rate in a single rate step. In other instances, the controller 24 may return to pace the ventricle of the patient's heart at the therapy based pacing rate increasingly over time (step-wise, logarithmic, linear ramp, etc.)

In some cases, a single reduction in the pacing rate may not be sufficient to permit intrinsic beats to occur and be detected by the IMD 12. For example, if there are not sustained intrinsic beats at the first reduced pacing rate, the controller 24 may be configured to identify a second reduced pacing rate representing a reduction relative to the first reduced pacing rate and may pace the ventricle of the patient's heart for a period of time at the second reduced pacing rate using a plurality of pacing pulses, but where one or more of the plurality of pacing pulses may be inhibited by a corresponding sensed intrinsic beat. The controller 24 may determine if there are sustained intrinsic beats at the second reduced pacing rate. If there are sustained intrinsic beats at the second reduced pacing rate, the controller 24 may be configured to return to pace the ventricle of the patient's heart at the therapy based pacing rate. However, if there are not sustained intrinsic beats at the second reduced pacing rate, the controller 24 may be configured to identify a third reduced pacing rate representing a reduction relative to the second reduced pacing rate and to pace the ventricle of the patient's heart for a period of time at the third reduced pacing rate using a plurality of pacing pulses, but where one or more of the plurality of pacing pulses may be inhibited by a corresponding sensed intrinsic beat. The controller 24 may determine if there are sustained intrinsic beats at the third reduced pacing rate. If there are sustained intrinsic beats at the third reduced pacing rate, the controller 24 may be configured to return to pace the ventricle of the patient's heart at the therapy based pacing rate. If not, it will be appreciated that the controller 24 may further reduce the pacing rate and continue the process until either sustained intrinsic beats are detected or a lower search rate limit is reached.

In some cases, while pacing, either at an initial pacing rate or at a reduced pacing rate, the controller 24 may be configured to record one or more items that may be related to cardiac activity, or that may provide an indication of cardiac health. In some cases, the controller 24 may record over time, such as during a period of time in which the controller 24 is pacing at a particular rate. Illustrative but non-limiting examples of items that the controller 24 may record include a beat type for each beat, such as whether each beat is an intrinsic beat or a paced beat, a beat rate that represents the rate at which the beats occur, a beat rate variability that represents the rate variability at which the beats occur, and an egram. Additional items that the controller 24 may record include a respiration rate parameter, a posture parameter, one or more heart sound parameters, one or more contractility parameters, a QRS width parameter, a PR interval parameter, a QRS to S1 interval parameter, a blood pressure parameter, an activity level parameter, an AV delay parameter, and a p-wave indicator. In some cases, the IMD 12 may be configured to transmit one or more of these items to the remote device 14 (FIG. 1).

Figure 3:
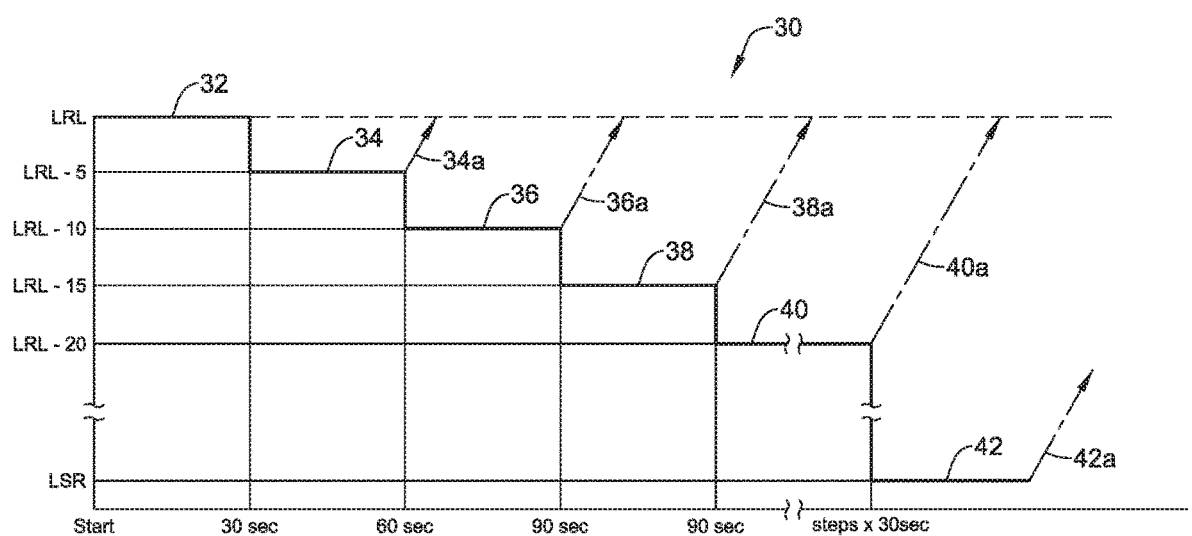
FIG. 3 is a timing diagram of an illustrative intrinsic beat search algorithm beginning at a lower rate limit of the IMD of FIG. 1 in accordance with an example of the disclosure.

FIG. 3 is a timing diagram that illustrates how the IMD 12 may function in performing an intrinsic heart beat search algorithm. In some cases, the intrinsic heart beat algorithm may begin at a therapy-based pacing rate. In some cases, as shown in FIG. 3, the therapy-based pacing rate may represent a lower rate limit (LRL) of the IMD 12. The LRL may represent the minimum pacing rate of the pacemaker, and may be used when the patient is at rest.

In some instances, as will be described with respect to FIG. 4, the therapy-based pacing rate may be based at least in part on patient activity. For example, the therapy-based pacing rate may be a sensor indicated rate. In some cases, the controller 24 may perform an intrinsic beat search algorithm at each of two or more different therapy based pacing rates (e.g. at two or more different patient activity levels). In some cases, the controller 24 may be configured to record one or more items at each of the reduced pacing rates when performing the intrinsic heart beat search algorithm shown in FIG. 3 and FIG. 4.

It will be appreciated that any numerical data shown in the timing diagram is merely illustrative, and is not intended to be limiting in any way. The timing diagram 30 of FIG. 3 shows the pacing rate on the vertical axis and time on the horizontal axis. The intrinsic heart beat search algorithm begins with the IMD 12 pacing at a lower rate limit (LRL) for a period of time, as indicated at 32. After a period of time, which is 30 seconds in this example, the controller 24 drops the pacing rate to a reduced pacing rate of LRL-5, which represents a reduction of 5 beats per minute in the pacing rate, as indicated at 34. The IMD 12 then looks for sustained intrinsic beats at this rate, and if detected, the controller 24 returns to pacing at the LRL rate, as indicated by arrow 34a. If sustained intrinsic beats is not detected, the controller 24 drops the pacing rate again to a further reduced pacing rate of LRL-10, which represents a further reduction of 5 beats per minute in the pacing rate, as indicated at 36.

If sustained intrinsic beats are detected at 36, the controller 24 returns to pacing at the LRL rate, as indicated by arrow 36a. If not, the controller 24 drops the pacing rate again to a further reduced pacing rate of LRL-15, which represents a further reduction of 5 beats per minute in the pacing rate, as indicated at 38. If sustained intrinsic beats are detected at 38, the controller 24 returns to pacing at the LRL rate, as indicated by arrow 38a. If not, the controller 24 drops the pacing rate again to a further reduced pacing rate of LRL-20, which represents a further reduction of 5 beats per minute in the pacing rate, as indicated at 40. If sustained intrinsic beats are detected at 40, the controller 24 returns to pacing at the LRL rate, as indicated by arrow 40a. If not, the controller 24 may continue to drop the pacing rate, looking for sustained intrinsic beats, until sustained intrinsic beats are detected or the controller 24 is pacing at a lower search rate limit (LSR), as indicated at 42. The controller 24 may then return to the LRL rate, as indicated by arrow 42a. It is contemplated that returning to the LRL rate at 34a, 36a, 38a, 40a and 42a may occur in a single step, or may increase over time (step-wise, logarithmic, linear ramp, etc.).

Figure 4:
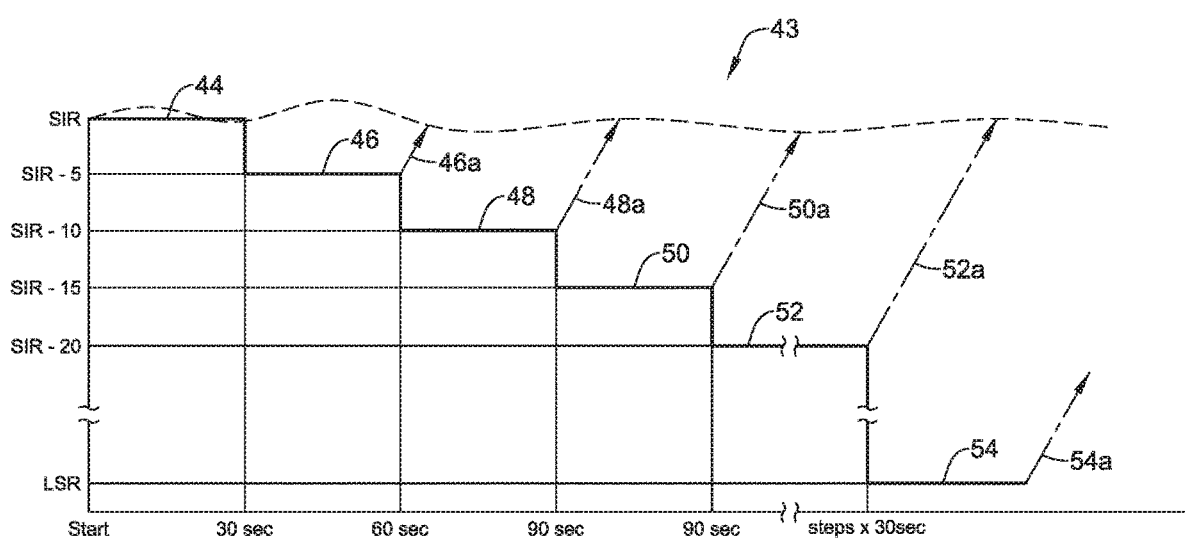
FIG. 4 is a timing diagram of another illustrative intrinsic beat search algorithm beginning at a therapy based pacing rate of the IMD of FIG. 1 based on a patient activity level in accordance with an example of the disclosure.

FIG. 4 is a timing diagram 43 that illustrates how the IMD 12 may function in performing an intrinsic heart beat search algorithm that is based on a sensor indicated rate (SIR). In some cases, the intrinsic heart beat search algorithm may be performed at one or several different patient activity levels to collect items across various patient activity levels. In some instances, the patient activity level may be determined in any number of ways, although in some cases the IMD 12 may include an accelerometer to directly provide an indication of patient activity. In some cases, other indications such as posture, respiration (including rate, rhythm, tidal volume, minute ventilation and others), and/or other parameters may be used as an indication of patient activity. In some cases, the intrinsic heart beat search algorithm is performed at several different activity levels (i.e. several different SIR values). For example, the intrinsic heart beat search algorithm may be performed at an SIR of 80, 90, 100, 120 and 140. These are just examples.

It will be appreciated that any numerical data shown in the timing diagram 43 is merely illustrative, and is not intended to be limiting in any way. The timing diagram 43 shows a pacing rate on the vertical axis and time on the horizontal axis. The timing diagram 43 begins with the IMD 12 pacing at a sensor indicated rate (SIR) for a period of time, as indicated at 44. After a period of time, which is 30 seconds in this example, the controller 24 drops the pacing rate to a reduced pacing rate of SIR-5, which represents a reduction of 5 beats per minute in the pacing rate, as indicated at 46. If sustained intrinsic beats are detected, the controller 24 returns to pacing at the SIR rate, as indicated by arrow 46a. If not, the controller 24 drops the pacing rate again to a further reduced pacing rate of SIR-10, which represents a further reduction of 5 beats per minute in the pacing rate, as indicated at 48. If sustained intrinsic beats are detected, the controller 24 returns to pacing at the SIR rate, as indicated by arrow 48a. If not, the controller 24 drops the pacing rate again to a further reduced pacing rate of SIR-15, which represents a further reduction of 5 beats per minute in the pacing rate, as indicated at 50. If sustained intrinsic beats are detected, the controller 24 returns to pacing at the SIR rate, as indicated by arrow 50a. If not, the controller 24 drops the pacing rate again to a further reduced pacing rate of SIR-20, which represents a further reduction of 5 beats per minute in the pacing rate, as indicated at 52. If sustained intrinsic beats are detected, the controller 24 returns to pacing at the LRL rate, as indicated by arrow 52*a*. If not, the controller 24 may continue to drop the pacing rate, looking for sustained intrinsic beats, until sustained intrinsic beats are detected or the controller 24 is pacing at the lower search rate (LSR), as indicated at 54. In some cases, the LSR may be different from the LRL, and may be based at least in part upon a current sensor indicated rate (SIR). The controller 24 may then return to the SIR rate, as indicated by arrow 54*a*. While the pacing rate is shown decreasing in a step-wise manner in FIGS. 3 and 4, it is contemplated that the pacing rate may be changed in any other suitable manner such as a Fibonacci search pattern.

The above examples assumes that the IMD 12 is pacing the ventricle at a set pacing rate and asynchronous relative to the atrial contractions feeding the ventricle. However, in some cases, the IMD 12 may have the capability to sense an atrial contraction (e.g. via p-wave, atrial pressure kick, heart sounds, etc.), the IMD 12 may pace the ventricle at an AV delay after each atrial contraction. When so provided, the controller 24 may be configured to perform an intrinsic heart beat search by adjusting the AV delay, rather than adjusting the pacing rate. In some cases, the controller 24 may be configured to pace the ventricle of the patient's heart using an initial AV delay after each atrial contraction for a plurality of cardiac cycles, but where one or more of the plurality of pacing pulses may be inhibited by a corresponding sensed ventricular intrinsic beat. The controller 24 may be configured to perform an intrinsic beat search algorithm during which the controller 24 identifies a first AV delay that is longer than the initial AV delay and paces the ventricle of the patient's heart H using the first AV delay after each atrial contraction for a plurality of cardiac cycles. The controller 24 may determine if there is atrioventricular conduction (as indicated by sustained intrinsic beats) using the first AV delay.

If there are sustained intrinsic beats at the first AV delay, the controller 24 may be configured to return to pace the ventricle of the patient's heart using the initial AV delay. However, if sustained intrinsic beats are not detected, the controller 24 may be configured to identify a second AV delay that is longer than the first AV delay and to pace the ventricle of the patient's heart using the second AV delay after each atrial contraction for a plurality of cardiac cycles. The controller 24 may determine if there are sustained intrinsic beats using the second AV delay. If so, the controller 24 may be configured to return to pace the ventricle of the patient's heart H using the initial AV delay. It will be appreciated that this may continue until either sustained intrinsic beats are detected or the AV delay becomes excessive, such as becomes greater than an AV delay search limit.

Figure 5:
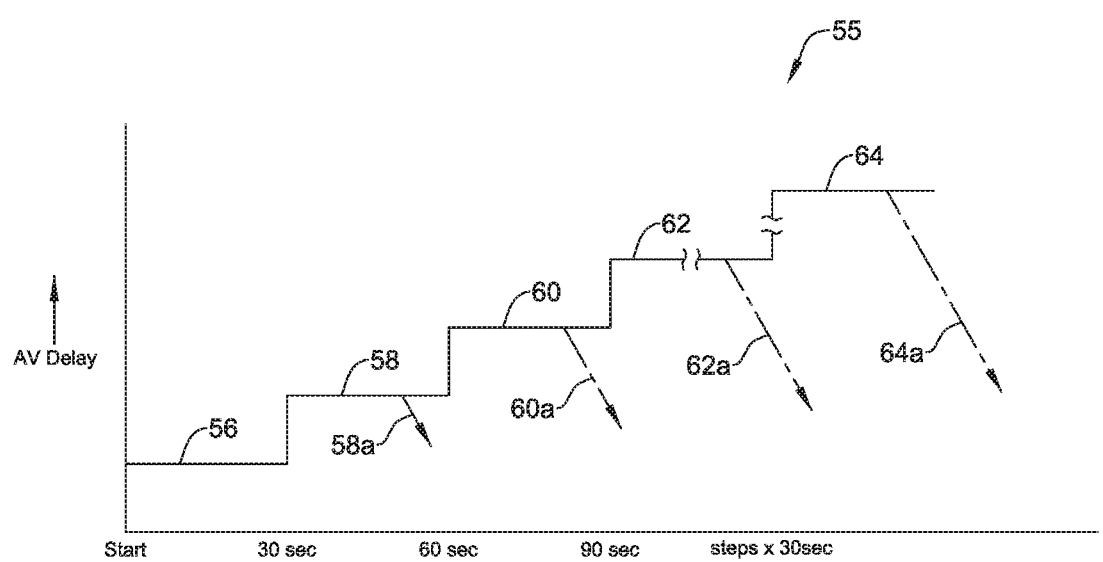
FIG. 5 is a timing diagram of an illustrative intrinsic beat search algorithm based on changes in AV delay in accordance with an example of the disclosure.

FIG. 5 is a timing diagram 56 that illustrates how the IMD 12 may function in performing an intrinsic heart beat search algorithm using a varying AV delay. The timing diagram 56 shows an AV delay on the vertical axis and time on the horizontal axis. The timing diagram 56 begins with the IMD 12 pacing with an initial AV delay for a period of time, as indicated at 56. After a period of time, which is 30 seconds in this example, the controller 24 increases the AV delay to a second AV delay, as indicated at 58. If sustained intrinsic beats are detected, the controller 24 returns to pacing at the initial AV delay, as indicated by arrow 58*a*. If not, the controller 24 increases to a third AV delay, as indicated at 60. If sustained intrinsic beats are detected, the controller 24 returns to pacing at the original AV delay rate, as indicated by row 60*a*. If not, the controller 24 increases to a fourth AV delay, as indicated at 62. If sustained intrinsic beats are detected, the controller 24 returns to pacing at the original AV delay, as indicated by arrow 62*a*. If not, the controller 24 increases the AV delay again, as indicated at 64. If sustained intrinsic beats are detected, the controller 24 returns to pacing at the original AV delay, as indicated by arrow 64*a*. This may continue until either sustained intrinsic beats are detected or an AV delay search limit is reached. While the AV delay is shown increasing in a step-wise manner, it is contemplated that the AV delay may be changed in any other suitable manner such as a Fibonacci search pattern.

Figure 6:
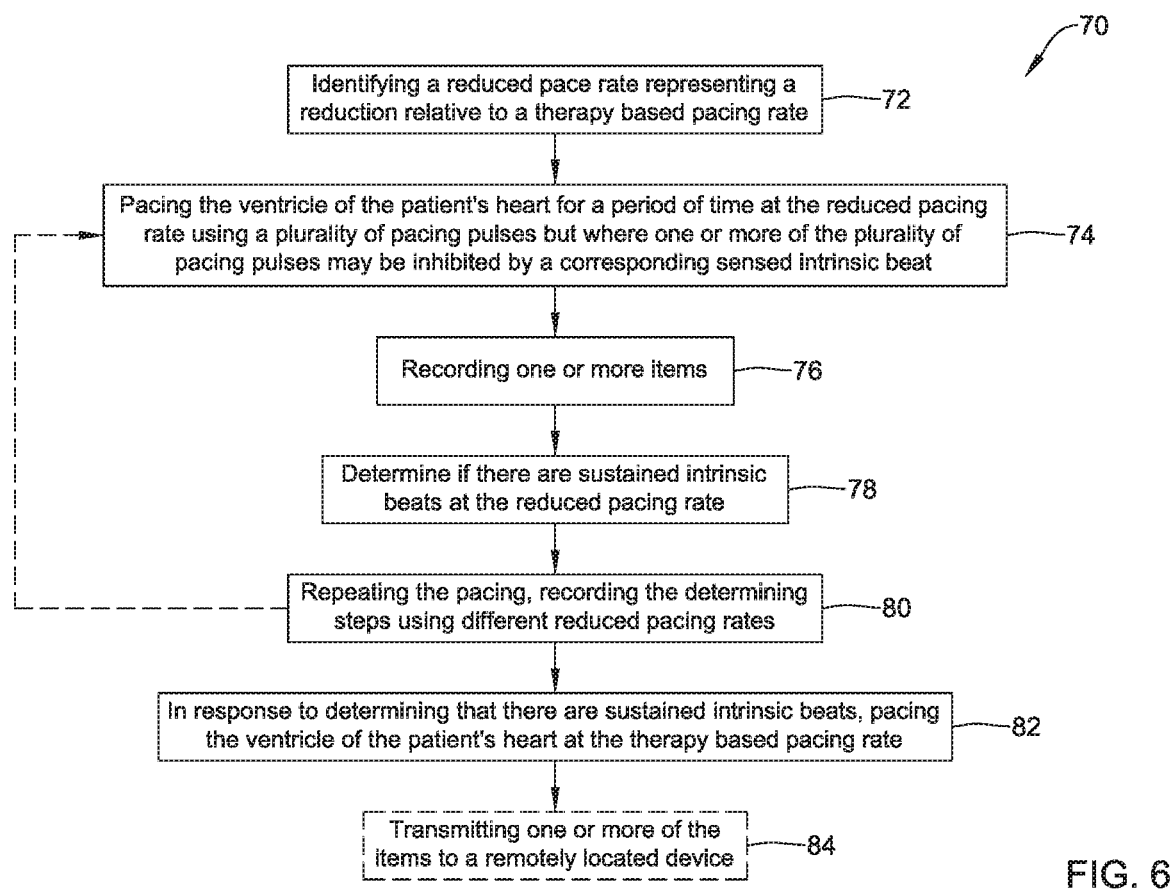
FIG. 6 is a flow diagram showing an illustrative method of performing an intrinsic heart beat search while delivering pacing therapy in accordance with an example of the disclosure.

FIG. 6 is a flow diagram 70 that shows an illustrative method of performing an intrinsic heart beat search in an implantable medical device (such as the IMD 12) while delivering pacing therapy to a patient's heart. A reduced pacing rate representing a reduction relative to a therapy based pacing rate may be identified, as indicated at block 72. The ventricle of the patient's heart may be paced for a period of time at the reduced pacing rate using a plurality of pacing pulses but where one or more of the plurality of pacing pulses may be inhibited by a corresponding sensed intrinsic beat, as seen at block 74. As indicated at block 76, one or more items may be recorded. These items may include, for example, one or more of a beat type for each beat that indicates whether each beat is an intrinsic beat or a paced beat, a beat rate that represents the rate at which the beats occur, a beat rate variability that represents the rate variability at which the beats occur, and an egram. As indicated at block 78, a determination may be made as to if there are sustained intrinsic beats at the reduced pacing rate. If necessary, the pacing, recording and determining steps may be repeated using different reduced pacing rates, as indicated at block 80. Once a determination has been made that there are sustained intrinsic beats, the ventricle of the patient's heart may be paced at the therapy based pacing rate, as indicated at block 82. Optionally, as shown at block 84, one or more of the recorded items may be transmitted to a remotely located device (such as the remote device 14 of FIG. 1).

Figure 7:
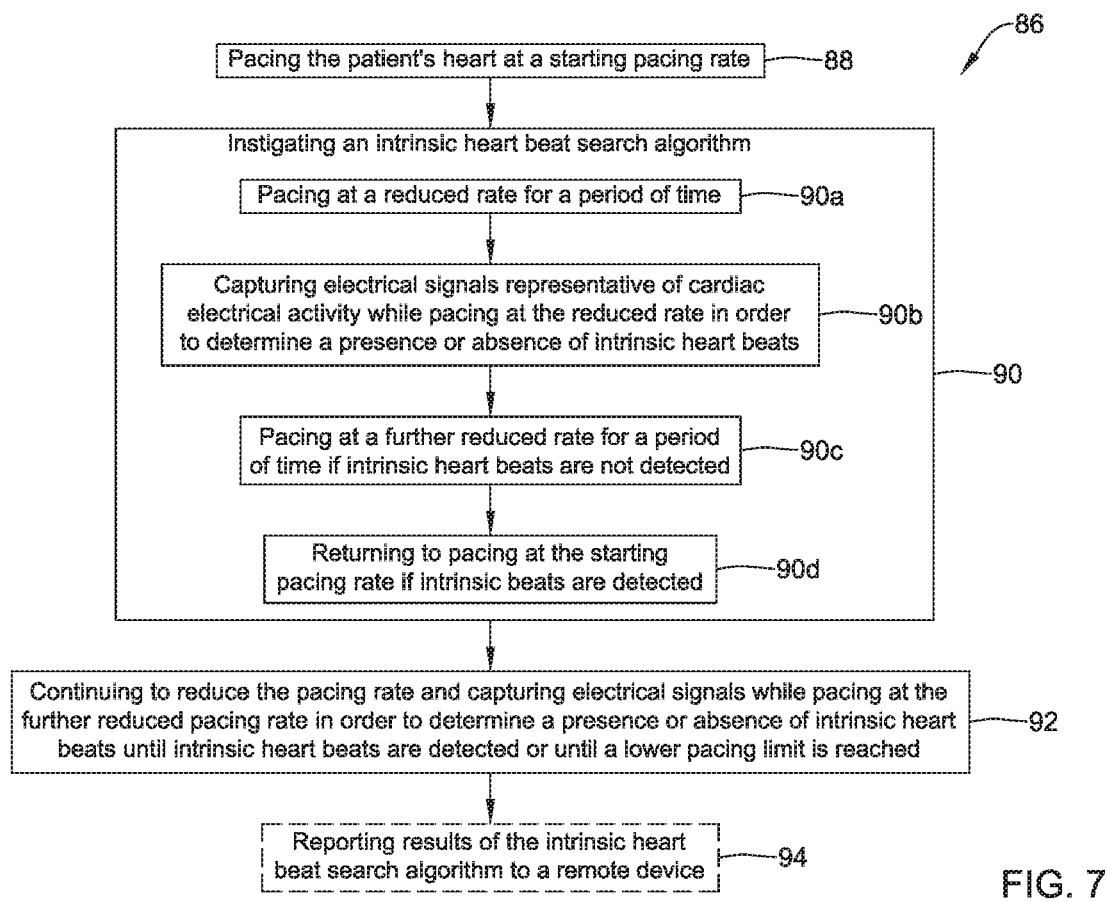
FIG. 7 is a flow diagram showing another illustrative method of regulating cardiac activity following a procedure that may temporarily impair a cardiac conduction system in accordance with an example of the disclosure.

FIG. 7 is a flow diagram 86 that shows a method of regulating cardiac activity following a procedure that may temporarily impair a cardiac conduction system within a patient's heart. In some cases, for example, procedures such as trans-catheter valve replacement may temporarily damage the cardiac conduction system within the patient's heart. In some cases, it may be desirable to periodically check to see how well the heart is doing on its own by conducting an intrinsic heart beat search. As indicated at block 88, the patient's heart may be paced at a starting pacing rate. An intrinsic heart beat search algorithm may be instigated, as indicated at block 90. In some cases, as illustrated, the intrinsic heart beat search algorithm includes pacing at a reduced rate for a period of time, as shown at block 90*a*, and capturing electrical signals representative of cardiac electrical activity while pacing at the reduced rate in order to determine a presence or absence of intrinsic heart beats as indicated at block 90*b*. As seen at block 90*c*, pacing may continue at a further reduced rate for a period of time if intrinsic heart beats are not detected. If intrinsic beats are detected, pacing may return to the starting pacing rate as indicated at block 90*d*. The method continues at block 92, in continuing to reduce the pacing rate and capturing electrical signals while pacing at the further reduced pacing rate in order to determine a presence or absence of intrinsic heart beats until intrinsic heart beats are detected or until a lower pacing rate limit is reached. Optionally, as shown at block 94, the results of the intrinsic heart beat search algorithm may be reported to a remote device.

Figure 8:
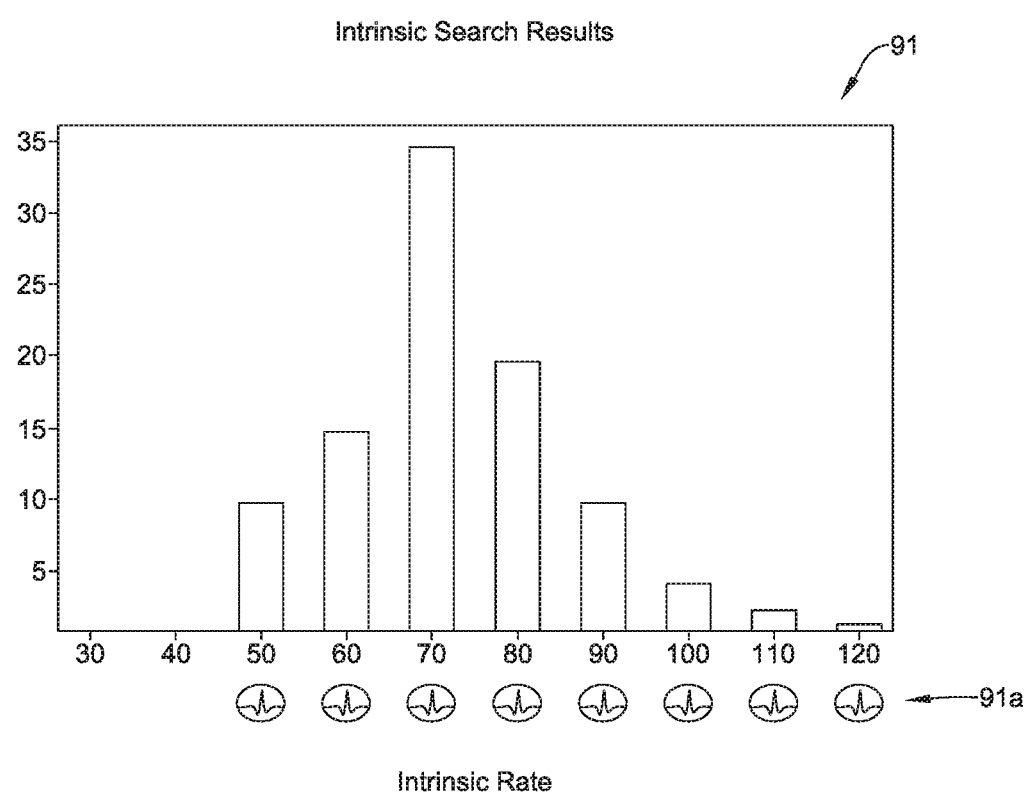
FIGS. 8 through 10 are illustrative graphical representations of histograms that may be displayed by the remote device of FIG. 1, based on data from the IMD of FIG. 1 in accordance with an example of the disclosure.
Figure 9:
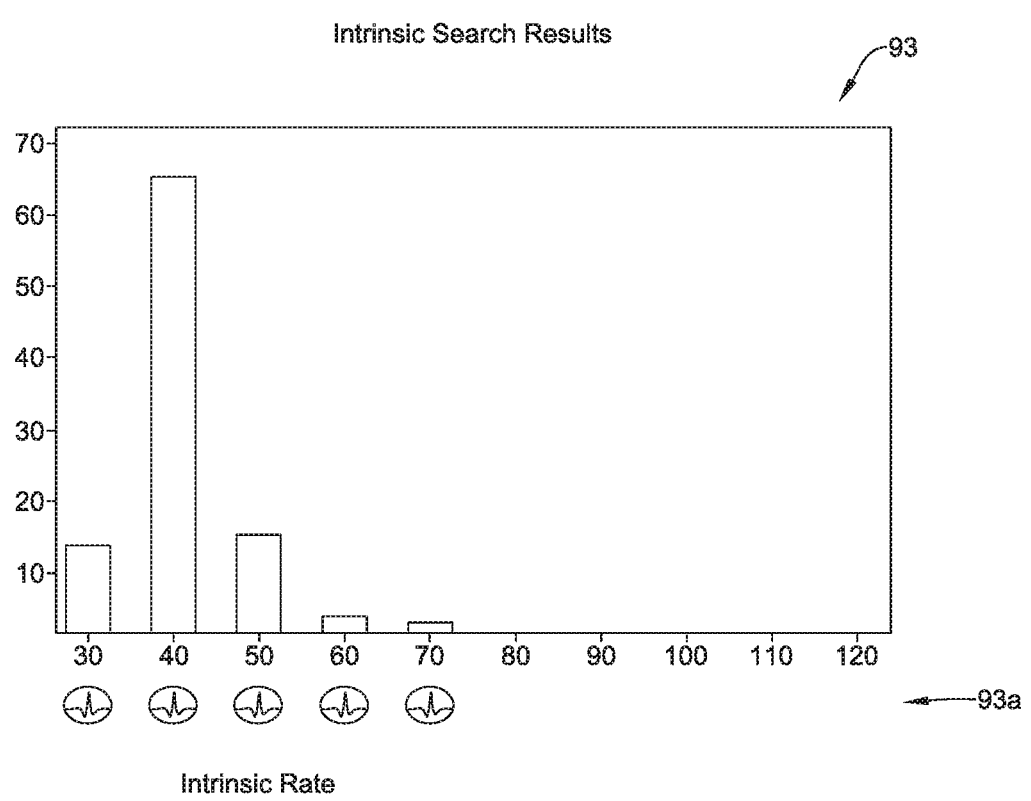
Figure 10:
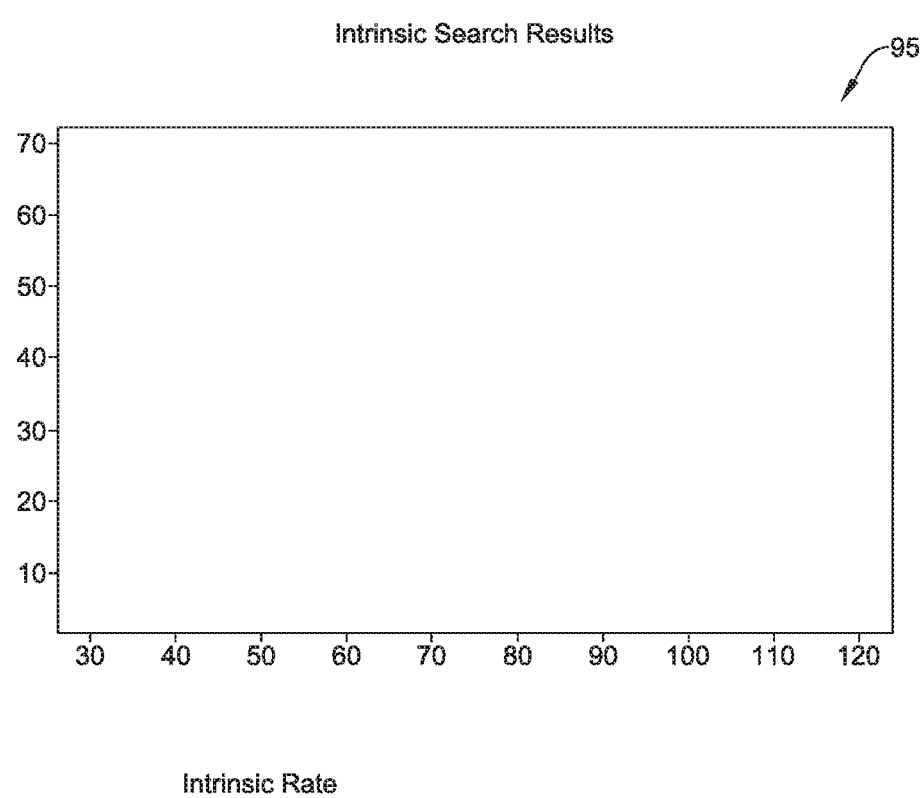

It will be appreciated that the IMD 12 may be recording a variety of different cardiac-related items while pacing, and while conducting an intrinsic heart beat search. This data may be transmitted to a remote device such as the remote device 14 (FIG. 1) so that the remote device can further process the data, if necessary, and then display the data so that a physician or other medical professional may review the data. FIGS. 8 through 10 provide illustrative but non-limiting examples of charts that may be displayed on a remote device, using data provided by the IMD 12.

FIGS. 3 through 7 provide examples of using sustained intrinsic beat detection in order to characterize the state of the heart's conduction system. In some cases, other cardiac parameters may be used in addition to, or instead of, sustained intrinsic beat detection. For example, the morphology of the QRS waveform may be used to characterize the state of the heart's conduction system. In some cases, relatively narrow or wide waveforms indicate depolarization originating in an atria or a ventricle, respectively. In another example, the duration of the PR interval may be used to characterize the state of the heart's conduction system wherein relatively short or long duration indicates normal or abnormal, respectively, atrioventricular conduction.

FIG. 8 shows a histogram 91 that shows number of occurrences on the vertical axis and heart rates on the horizontal axis. The histogram 91 may represent a compilation from one or more executions of the intrinsic heart beat search algorithm. In looking at the numbers, which are merely illustrative, it can be seen in the histogram 91 that there were a total of 10 instances of intrinsic heart beats at a heart rate of 50 beats per minute (bpm), 15 instances at a heart rate of 60 bpm, 35 instances at a heart rate of 70 bpm, 20 instances at a heart rate of 80 bpm, 10 instances at 90 bpm, and decreasing instances at heart rates of 100 bpm and above. The paced beats are not shown on this histogram 91, but they could be shown as a separate bar if desired. In some cases, the data at the lower heart rates may be obtained using an algorithm starting with an LRL (as shown for example in FIG. 3) while the data at the higher heart rates may be obtained using an algorithm starting with an SIR at a higher patient activity level (as shown for example in FIG. 4).

The histogram 91 includes a row of icons 91a, with a number of icons each arranged under a corresponding bar graph portion for a particular heart rate. These icons 91a may represent touch buttons, for example, that may be selected to instruct the remote device 14 to display additional data, such as but not limited to the cardiac related items discussed previously, including collected egrams that correspond to that heart rate. It will be appreciated that the histogram 91 represents data for a patient with a relatively healthy heart producing substantial intrinsic heart beats at or around 70 beats per minute.

FIG. 9 shows a histogram 93 that shows number of occurrences on the vertical axis and heart rates on the horizontal axis. The histogram 93 may represent a compilation from one or more executions of the intrinsic heart beat search algorithm. In looking at the numbers, which are merely illustrative, it can be seen in the histogram 93 that there were a total of about 15 instances of intrinsic heart beats at a heart rate of 30 bpm, over 60 instances at a heart rate of 40 bpm, about 15 instances at a heart rate of 50 bpm and decreasing instances at heart rates at 60 bpm and above. The paced beats are not shown on this histogram 93, but they could be shown as a separate bar if desired. The histogram 93 includes a row of icons 93a, with a number of icons each arranged under a corresponding bar graph portion for a particular heart rate. These icons 93a may represent touch buttons, for example, that may be selected to instruct the remote device 14 to display additional data, such as but not limited to the cardiac related items discussed previously, including collected egrams that correspond to that heart rate. It will be appreciated that the histogram 93 represents data for a patient with a relatively unhealthy heart producing very few intrinsic heart beats at a safe heart rate (e.g. 60 beats per minute).

FIG. 10 shows a histogram 95 that shows number of occurrences on the vertical axis and heart rates on the horizontal axis. The histogram 95 may represent a compilation from one or more executions of the intrinsic heart beat search algorithm. The feature that stands out in the histogram 95 is that there are no detected intrinsic heart beats, as indicated by the histogram 95 being blank. It will be appreciated that the histogram 95 represents data for a patient with a unhealthy heart producing no detectable intrinsic heart beats. That is, all heart beats are paced heart beats across the entire range of heart beats.

Figure 11:
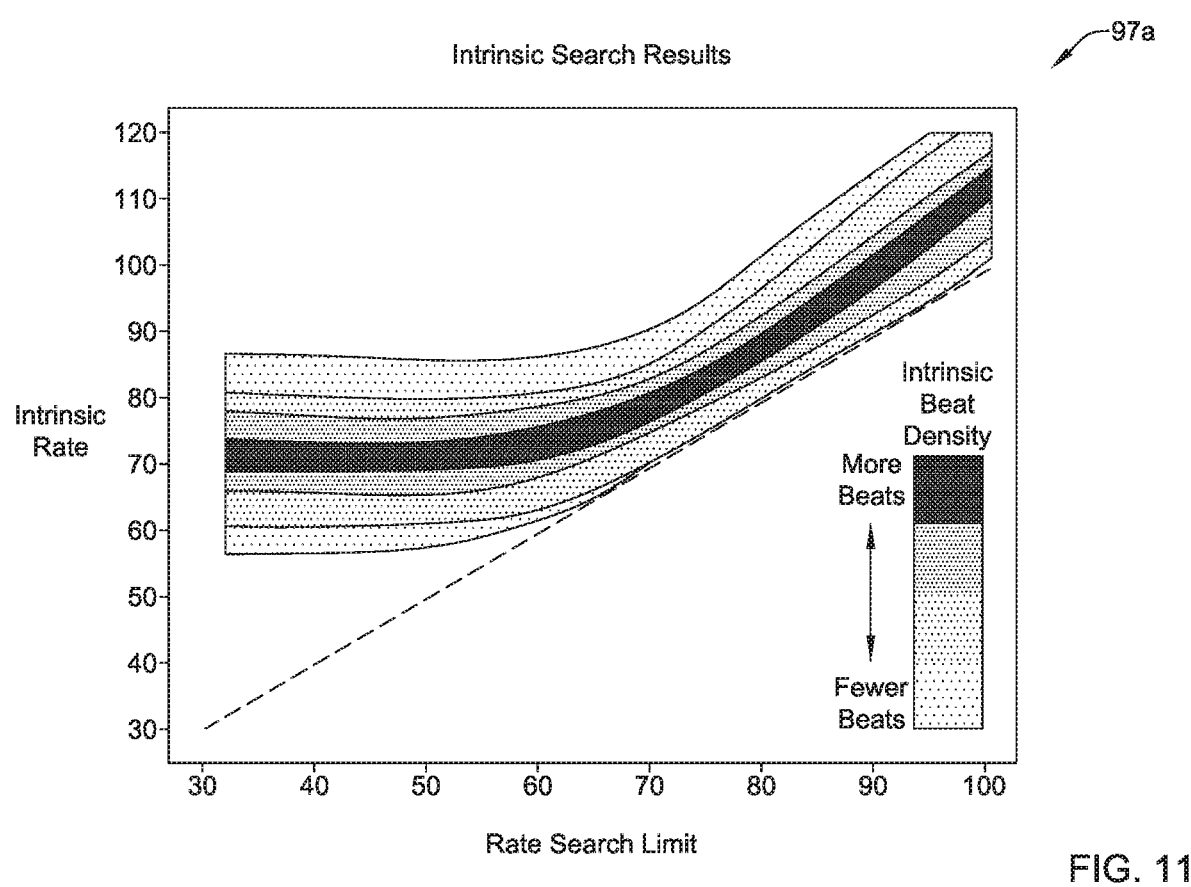
FIGS. 11 through 14 are illustrative graphical representations of charts that may be displayed by the remote device of FIG. 1, based on data from the IMD of FIG. 1 in accordance with an example of the disclosure.

FIGS. 11 through 14 provide illustrative but non-limiting examples of charts that may be displayed on a remote device, using data provided by the IMD 12. Any numerical data represented is intended to be merely illustrative and is not intended to be limiting in any fashion. FIG. 11 shows a chart 97a in which the vertical axis represents an intrinsic heart rate while the horizontal axis represents a rate search limit. Anything above the dashed line represents intrinsic beats. The chart 97a shows significant intrinsic beats at all searched heart rates. This represents a healthy heart, and may for example correspond to the histogram 91 shown in FIG. 8.

Figure 12:
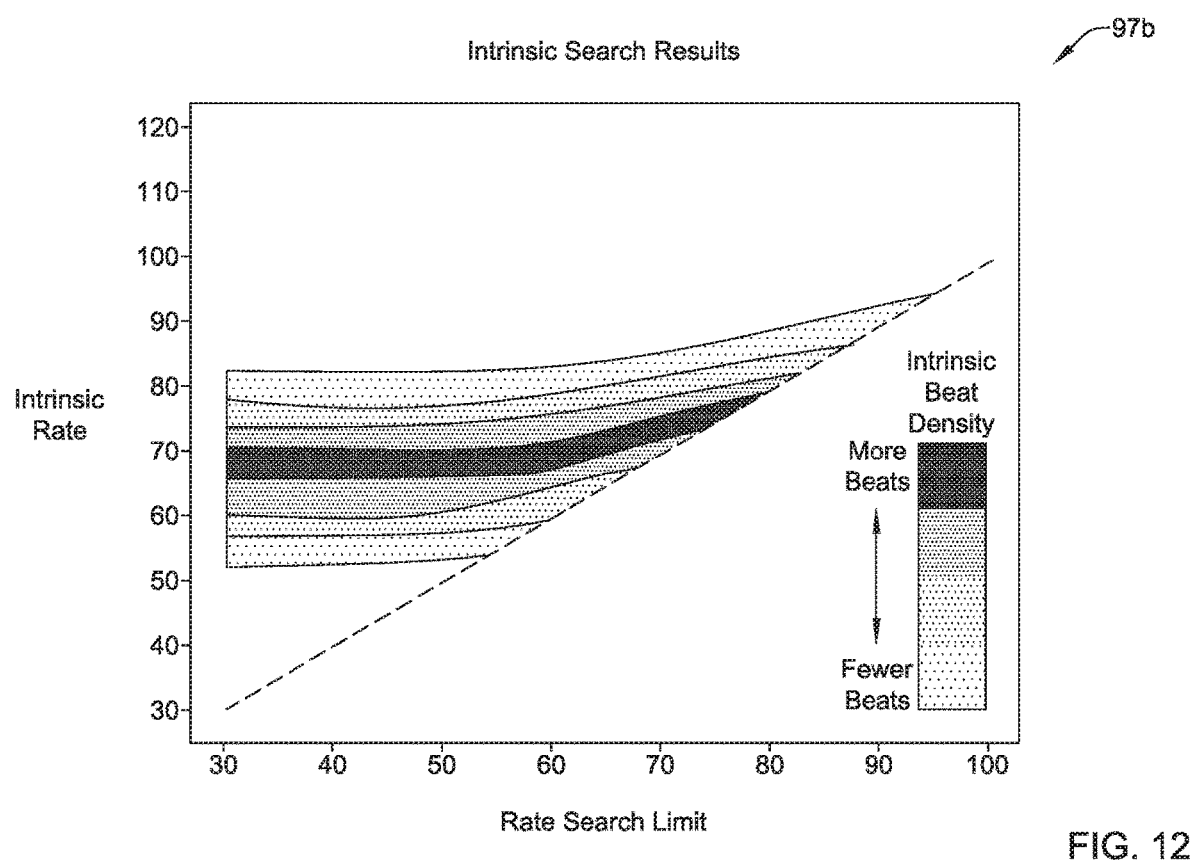
Figure 13:
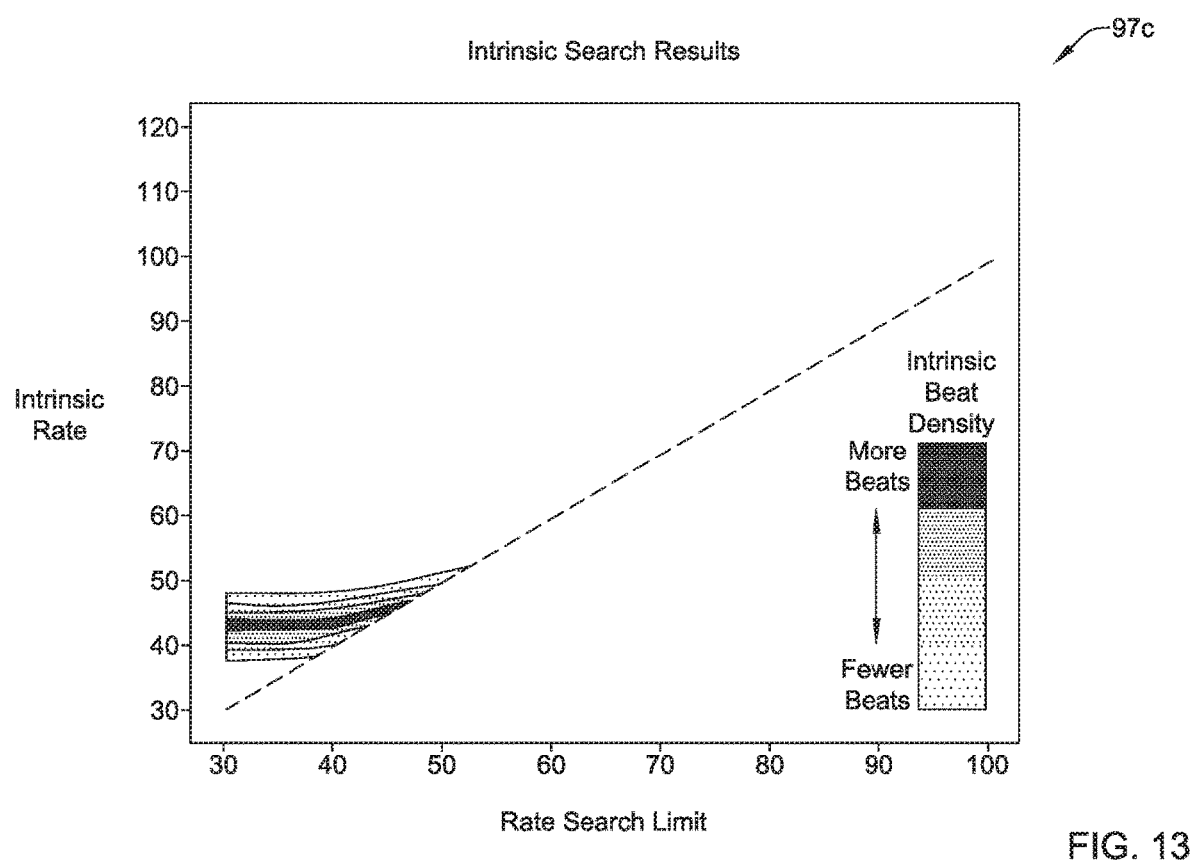
Figure 14:
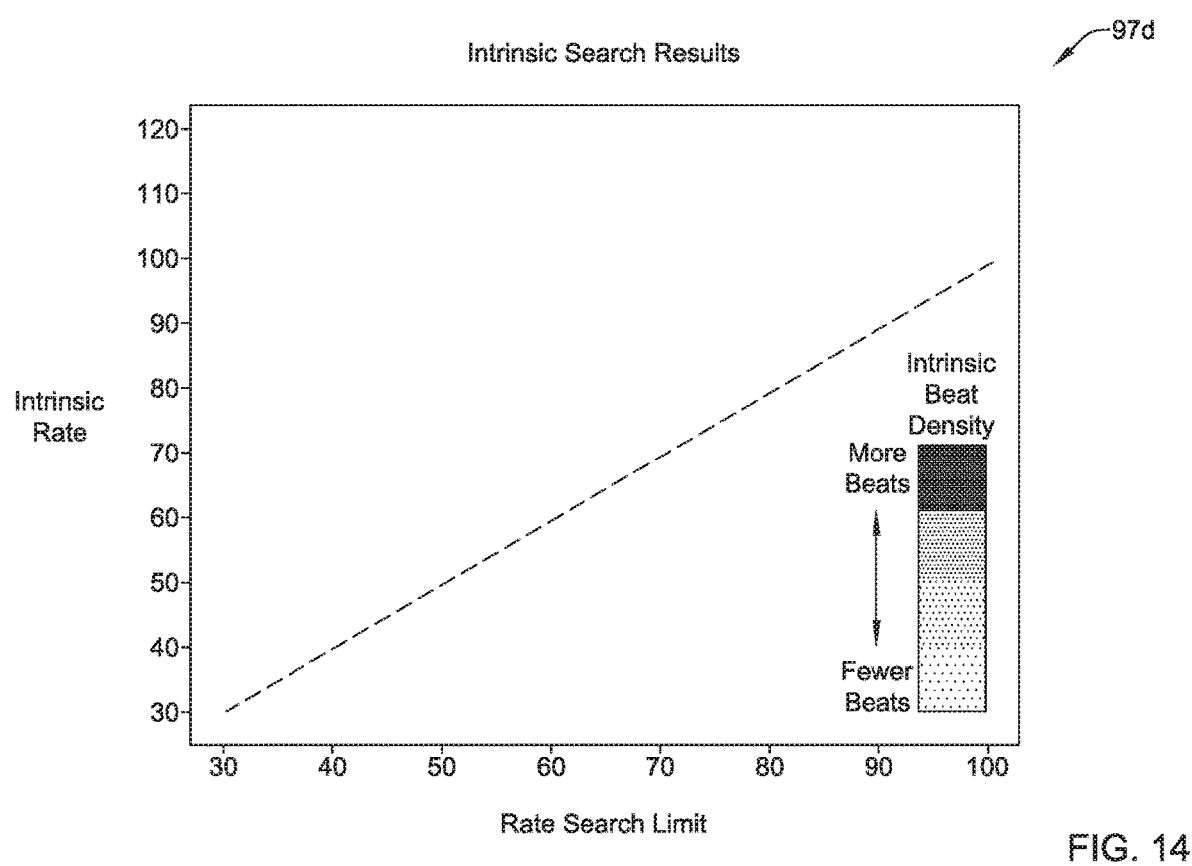

FIG. 12 shows a chart 97b that shows good intrinsic heart beats at low heart rates, indicating good conduction at low heart rates, but no intrinsic heart beats at high heart rates, indicating a conduction block at higher heart rates. FIG. 13 shows a chart 97c with very few intrinsic heart beats, and only at very low heart rates. This may represent a low ventricular escape rate, for example. FIG. 14 shows a chart 97d with absolutely no intrinsic beats detected. The chart 97d may be considered as corresponding to the histogram 95 (FIG. 10).

Figure 15:
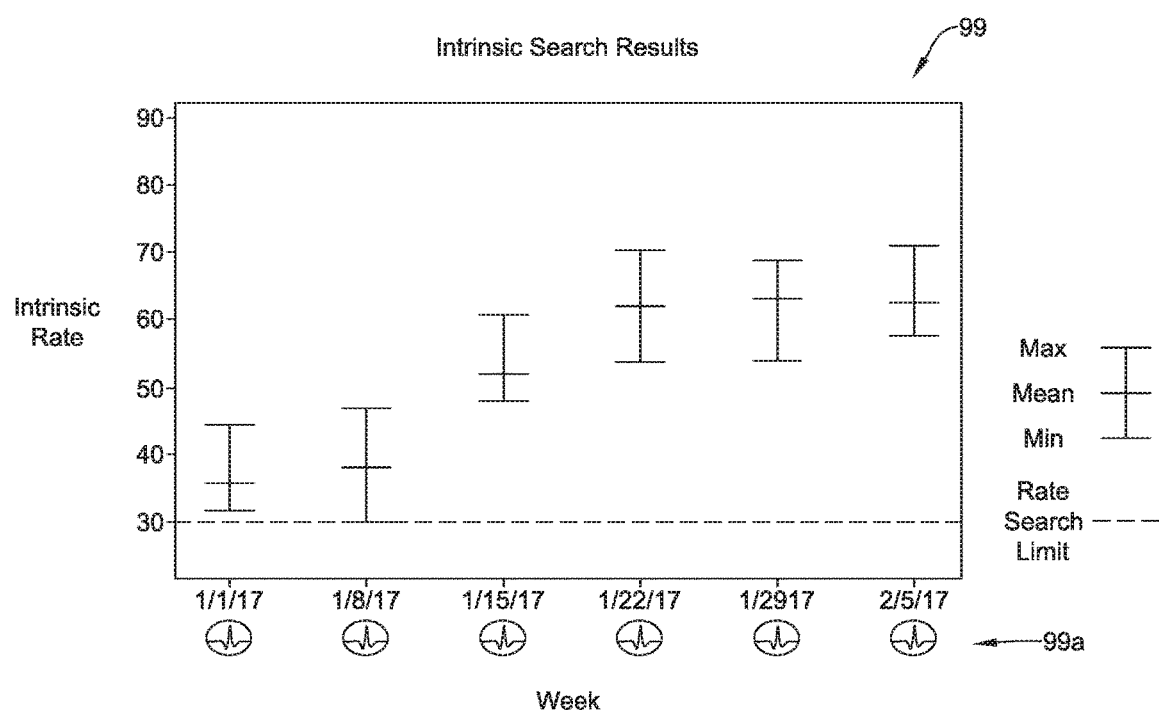
FIG. 15 is a graphical representation of a bar chart that may be displayed by the remote device of FIG. 1, based on data from the IMD of FIG. 1 in accordance with an example of the disclosure.

FIG. 15 provides an illustrative but non-limiting example of a bar chart 99 that may be displayed on a remote device, using data provided by the IMD 12. Any numerical data represented is intended to be merely illustrative and is not intended to be limiting in any fashion. In FIG. 15, the vertical axis represents intrinsic heart rate while the horizontal axis represents the passage of time. The bar chart 99 includes the max, min and mean intrinsic heart rate detected when performing one or more executions of the intrinsic heart beat search algorithm. The bar chart 99 shows data for a patient who initially had limited intrinsic beats (i.e. only at low heart rates), whether due to a temporary conduction problem or not, but over about the course of a month, the intrinsic rate stabilized with a mean intrinsic heart rate around 60 to 70 bpm. The bar chart 99 includes a row of icons 99a that may be used to display additional information pertaining to a particular date or period of time, as described above.

FIG. 16 depicts an illustrative leadless cardiac pacemaker (LCP) that may be implanted into a patient and may operate to deliver appropriate therapy to the heart, such as to deliver anti-tachycardia pacing (ATP) therapy, cardiac resynchronization therapy (CRT), bradycardia therapy, and/or the like. As can be seen in FIG. 16, the LCP 100 may be a compact device with all components housed within the or directly on a housing 120. In some cases, the LCP 100 may be considered as being an example of the IMD 12 (FIGS. 1 and 2). In the example shown in FIG. 16, the LCP 100 may include a communication module 102, a pulse generator module 104, an electrical sensing module 106, a mechanical sensing module 108, a processing module 110, a battery 112, and an electrode arrangement 114. The LCP 100 may include more or fewer modules, depending on the application.

The communication module 102 may be configured to communicate with devices such as sensors, other medical devices such as an SICD, another LCP, and/or the like, that are located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device (e.g. SICD and/or programmer) through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication.

In the example shown in FIG. 16, the pulse generator module 104 may be electrically connected to the electrodes 114. In some examples, the LCP 100 may additionally include electrodes 114'. In such examples, the pulse generator 104 may also be electrically connected to the electrodes 114'. The pulse generator module 104 may be configured to generate electrical stimulation signals. For example, the pulse generator module 104 may generate and deliver electrical stimulation signals by using energy stored in the battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate and deliver electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy. In some cases, the pulse generator 104 may provide a controllable pulse energy. In some cases, the pulse generator 104 may allow the controller to control the pulse voltage, pulse width, pulse shape or morphology, and/or any other suitable pulse characteristic.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' may represent ventricular cardiac electrical signals. In some cases, the LCP 100 may be configured to detect cardiac electrical signals from other chambers (e.g. far field), such as the P-wave from the atrium.

The mechanical sensing module 108 may include one or more sensors, such as an accelerometer, a pressure sensor, a heart sound sensor, a blood-oxygen sensor, a chemical sensor, a temperature sensor, a flow sensor and/or any other suitable sensors that are configured to measure one or more mechanical/chemical parameters of the patient. Both the electrical sensing module 106 and the mechanical sensing module 108 may be connected to a processing module 110, which may provide signals representative of the sensed mechanical parameters. Although described with respect to FIG. 16 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to the LCP 100 may have an insulative portion that electrically isolates the electrodes 114/114' from adjacent electrodes, the housing 120, and/or other parts of the LCP 100. In some cases, one or more of the electrodes 114/114' may be provided on a tail (not shown) that extends away from the housing 120.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, abnormalities in the operation of the heart H. Based on any determined abnormalities, the processing module 110 may control the pulse generator module 104 to generate and deliver electrical stimulation in accordance with one or more therapies to treat the determined abnormalities. The processing module 110 may further receive information from the communication module 102. In some examples, the processing module 110 may use such received information to help determine whether an abnormality is occurring, determine a type of abnormality, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 112 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

FIG. 17 depicts an example of another or second medical device (MD) 200, which may be used in conjunction with the LCP 100 (FIG. 16) in order to detect and/or treat cardiac abnormalities. In some cases, the MD 200 may be considered as an example of the IMD 12 (FIGS. 1 and 2), and may for example represent an implantable cardioverter defibrillator (ICD) or a subcutaneous implantable cardioverter defibrillator (SICD) that has the ability to pace the heart. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of LCP 100. Additionally, the battery 218 may be similar to the battery 112 of the LCP 100. In some examples, however, the MD 200 may have a larger volume within the housing 220. In such examples, the MD 200 may include a larger battery and/or a larger processing module 210 capable of handling more complex operations than the processing module 110 of the LCP 100.

While it is contemplated that the MD 200 may be another leadless device such as shown in FIG. 16, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously and outside of the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, acoustic sensors, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example the leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some examples, the MD 200 may additionally be configured provide defibrillation therapy.

In some instances, the MD 200 may be an implantable cardioverter-defibrillator (ICD) with the ability to pace. In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, the MD 200 may be a subcutaneous implantable cardioverter-defibrillator (S-ICD) with the ability to pace. In examples where the MD 200 is an S-ICD, one of the leads 212 may be a subcutaneously implanted lead. In some instances, the lead(s) may have one or more electrodes that are placed subcutaneously and outside of the chest cavity. In other examples, the lead(s) may have one or more electrodes that are placed inside of the chest cavity, such as just interior of the sternum but outside of the heart H.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy. In some cases, the MD 200 may be external to the patient's body may include a lead that extends transvenously into the heart. The lead may be used to sense and/or pace the heart.

Figure 18:
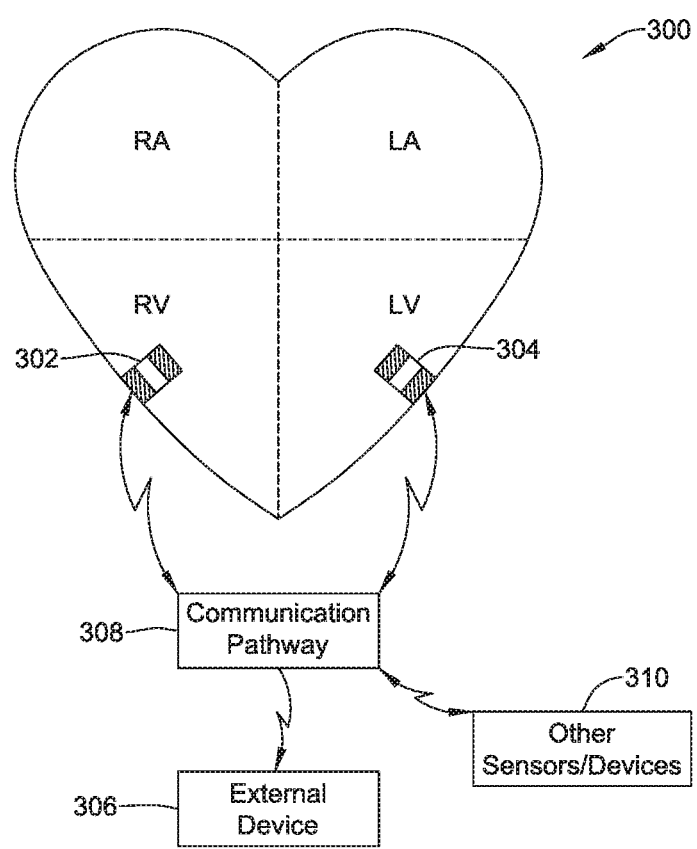
FIG. 18 is a schematic diagram of an illustrative medical system that includes multiple LCPs and/or other devices in communication with one another.

FIG. 18 illustrates an example of a medical device system and a communication pathway through which multiple medical devices 302, 304, 306, and/or 310 may communicate. In the example shown, the medical device system 300 may include LCPs 302 and 304, external medical device 306, and other sensors/devices 310. The external device 306 may be any of the devices described previously with respect to the MD 200. Other sensors/devices 310 may also be any of the devices described previously with respect to the MD 200. In some instances, other sensors/devices 310 may include a sensor, such as an accelerometer, an acoustic sensor, a blood pressure sensor, or the like. In some cases, other sensors/devices 310 may include an external programmer device that may be used to program one or more devices of the system 300.

Various devices of the system 300 may communicate via communication pathway 308. The communication pathway 308 may include one or a number of different communication paths and/or a number of different communication modes. The communication pathway 308 may also include one or more distinct communication vectors. In some cases, for example, the LCPs 302 and/or 304 may sense intrinsic cardiac electrical signals and may communicate such signals to one or more other devices 302/304, 306, and 310 of the system 300 via communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient. It is contemplated that the communication pathway 308 may communicate using RF signals, inductive coupling, optical signals, acoustic signals, or any other signals suitable for communication. Additionally, in at least some examples, device communication pathway 308 may include multiple signal types. For instance, other sensors/device 310 may communicate with the external device 306 using a first signal type (e.g. RF communication) but communicate with the LCPs 302/304 using a second signal type (e.g. conducted communication). Further, in some examples, communication between devices may be limited. For instance, as described above, in some examples, the LCPs 302/304 may communicate with the external device 306 only through other sensors/devices 310, where the LCPs 302/304 send signals to other sensors/devices 310, and other sensors/devices 310 relay the received signals to the external device 306.

In some cases, the communication pathway 308 may include conducted communication. Accordingly, devices of the system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of the system 300 may deliver electrical communication pulses at an amplitude/pulse width that is sub-capture threshold to the heart. Although, in some cases, the amplitude/pulse width of the delivered electrical communication pulses may be above the capture threshold of the heart, but may be delivered during a blanking period of the heart (e.g. refractory period) and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 19:
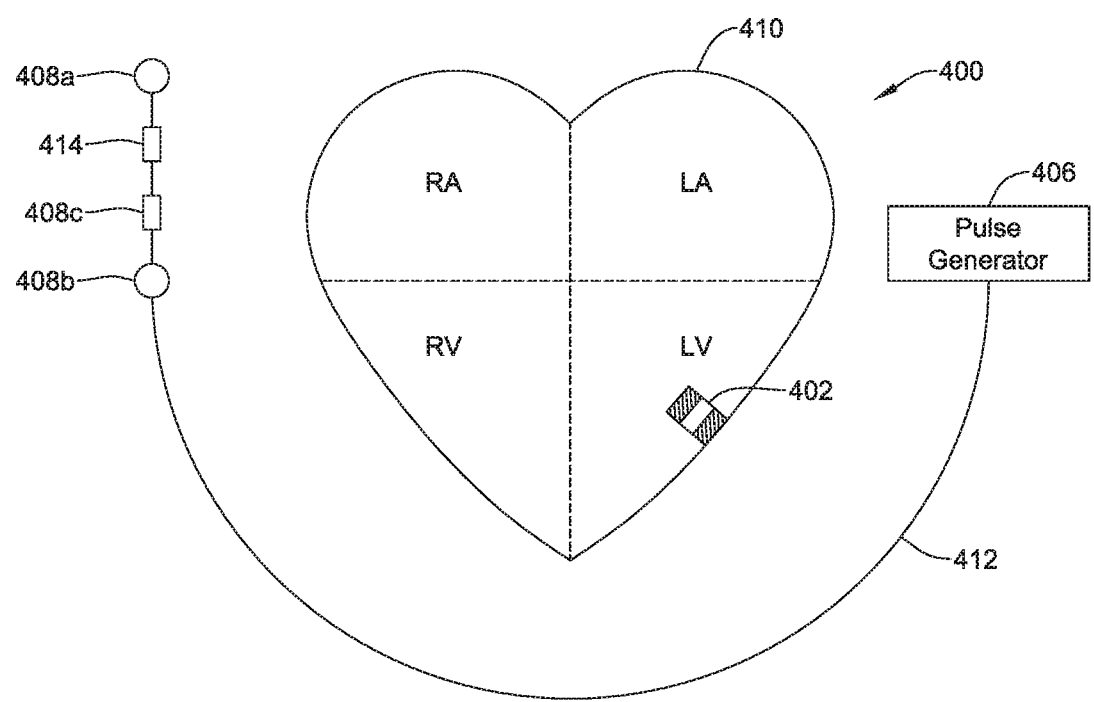
FIG. 19 is a schematic diagram of a system including an LCP and another medical device, in accordance with an example of the disclosure.

FIG. 19 shows an illustrative medical device system. In FIG. 19, an LCP 402 is shown fixed to the interior of the left ventricle of the heart 410, and a pulse generator 406 is shown coupled to a lead 412 having one or more electrodes 408a-408c. In some cases, the pulse generator 406 may be part of an implantable cardioverter defibrillator (ID) or a subcutaneous implantable cardioverter defibrillator (SICD), and the one or more electrodes 408a-408c may be positioned subcutaneously. In some cases, the one or more electrodes 408a-408c may be placed inside of the chest cavity but outside of the heart, such as just interior of the sternum. In some cases, the LCP 402 may communicate with the subcutaneous implantable cardioverter-defibrillator (SICD). In some cases, the lead 412 and/or pulse generator 406 may include an accelerometer 414 that may, for example, be configured to sense vibrations that may be indicative of heart sounds.

In some cases, the LCP 402 may be in the right ventricle, right atrium, left ventricle or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An implantable medical device (IMD) configured to sense electrical cardiac activity of a patient's heart and to pace a ventricle of the patient's heart, the IMD comprising:
    a housing;
    a plurality of electrodes;
    a controller disposed within the housing and operably coupled to the plurality of electrodes such that the controller can receive electrical signals from at least two of the plurality of electrodes representing electrical cardiac activity and can deliver pacing pulses to the ventricle of the patient's heart via at least two of the plurality of electrodes;
    a communications module operably coupled to the controller and configured to wirelessly communicate with a remotely located device;
    the controller is configured to pace the ventricle of the patient's heart at a therapy based pacing rate using a plurality of pacing pulses but where one or more of the plurality of pacing pulses may be inhibited by a corresponding sensed intrinsic beat;
    the controller is further configured to perform an intrinsic beat search algorithm during which the controller is configured to:
        identify a first reduced pacing rate representing a reduction relative to the therapy based pacing rate;
        pace the ventricle of the patient's heart for a period of time at the first reduced pacing rate using a plurality of pacing pulses but where one or more of the plurality of pacing pulses may be inhibited by a corresponding sensed intrinsic beat; and
        determine if there are sustained intrinsic beats at the first reduced pacing rate, wherein the controller determines that there are sustained intrinsic beats when at least 80 percent of the beats are intrinsic beats.

2. The IMD of claim 1, wherein if there is sustained intrinsic beats at the first reduced pacing rate, the controller is configured to return to pace the ventricle of the patient's heart at the therapy based pacing rate.

3. The IMD of claim 2, wherein the controller is configured to return to pace the ventricle of the patient's heart at the therapy based pacing rate in a single rate step.

4. The IMD of claim 2, wherein the controller is configured to return to pace the ventricle of the patient's heart at the therapy based pacing rate increasingly over time.

5. The IMD of claim 1, wherein if there is not sustained intrinsic beats at the first reduced pacing rate, the controller is configured to:
    identify a second reduced pacing rate representing a reduction relative to the first reduced pacing rate;
    pace the ventricle of the patient's heart for a period of time at the second reduced pacing rate using a plurality of pacing pulses but where one or more of the plurality of pacing pulses may be inhibited by a corresponding sensed intrinsic beat; and
    determine if there are sustained intrinsic beats at the second reduced pacing rate.

6. The IMD of claim 5, wherein if there is sustained intrinsic beats at the second reduced pacing rate, the controller is configured to return to pace the ventricle of the patient's heart at the therapy based pacing rate.

7. The IMD of claim 1, wherein the controller is configured to record one or more items over time.

8. The IMD of claim 7, wherein the controller is configured to transmit one or more of the items via the communications module to the remotely located device.

9. The IMD of claim 1, wherein the controller is further configured to record one or more items, the one or more items comprising one or more of:
    a beat type for each beat, wherein the beat type comprises an intrinsic beat or a paced beat;
    a beat rate, wherein the beat rate represents the rate at which the beats occur;
    a beat rate variability parameter, wherein the beat rate variability parameter represents the rate variability at which the beats occur;
    an egram;
    one or more respiration parameters;
    a posture parameter;
    one or more heart sound parameters;
    one or more contractility parameters;
    a QRS width parameter;
    a PR interval parameter
    a QRS to S1 interval parameter;
    a blood pressure parameter;
    an activity level parameter;
    an AV delay parameter; and
    a p-wave indicator.

10. The IMD of claim 1, wherein the controller determines that there are sustained intrinsic beats when at least 90 percent of the beats are intrinsic beats.

11. The IMD of claim 1, wherein the therapy based pacing rate is a lower rate limit.

12. The IMD of claim 1, wherein the therapy based pacing rate is above a lower rate limit and is based on a detected patient activity level.

13. The IMD of claim 12, wherein the controller is configured to perform the intrinsic beat search algorithm at each of two or more different therapy based pacing rates that are based on two or more different detected patient activity levels.

14. The IMD of claim 13, wherein the controller is further configured to record one or more items at each of the two or more different therapy based pacing rates, wherein the one or more items comprising one or more of:
- a beat type for each beat, wherein the beat type comprises an intrinsic beat or a paced beat;
- a beat rate, wherein the beat rate represents the rate at which the beats occur;
- a beat rate variability, wherein the beat rate variability represents the rate variability at which the beats occur; and
- an egram.

15. The IMD of claim 1, further comprising a battery having a battery capacity that is sufficient to power the IMD for 6 months or less when pacing at max pacing power at a rate of 60 beats/minute.

16. A method of performing an intrinsic heart beat search in an implantable medical device while delivering pacing therapy to a patient's heart, the method comprising:
- identifying a reduced pacing rate representing a reduction relative to a therapy based pacing rate;
- pacing a ventricle of the patient's heart for a period of time at the reduced pacing rate using a plurality of pacing pulses but where one or more of the plurality of pacing pulses may be inhibited by a corresponding sensed intrinsic beat;
- recording one or more items, the one or more items comprising one or more of:
  - a beat type for each beat, wherein the beat type comprises an intrinsic beat or a paced beat;
  - a beat rate, wherein the beat rate represents the rate at which the beats occur;
  - a beat rate variability, wherein the beat rate variability represents the rate variability at which the beats occur; and
  - an egram;
- determine if there are sustained intrinsic beats at the reduced pacing rate, wherein there is a determination of sustained intrinsic beats when at least 80 percent of the beats are intrinsic beats;
- repeating the pacing, recording and determining steps using different reduced pacing rates;
- in response to determining that there are sustained intrinsic beats, pacing the ventricle of the patient's heart at the therapy based pacing rate.

17. The method of claim 16, further comprising transmitting one or more of the items to a remotely located device.

18. A method of regulating cardiac activity following a procedure that may temporarily impair a cardiac conduction system within a patient's heart, the method comprising:
- pacing the patient's heart at a starting pacing rate;
- instigating an intrinsic heart beat search algorithm comprising:
  - pacing at a reduced rate for a period of time;
  - capturing electrical signals representative of cardiac electrical activity while pacing at the reduced rate in order to determine a presence or absence of sustained intrinsic heart beats, wherein there is a determination of sustained intrinsic beats when at least 80 percent of the beats are intrinsic beats;
  - pacing at a further reduced rate for a period of time if sustained intrinsic heart beats are not detected;
  - returning to pacing at the starting pacing rate if sustained intrinsic heart beats are detected;
  - continuing to reduce the pacing rate and capturing electrical signals while pacing at the further reduced pacing rate in order to determine a presence or absence of sustained intrinsic heart beats until sustained intrinsic heart beats are detected or until a lower search rate limit is reached.

19. The method of claim 18, further comprising reporting results of the intrinsic heart beat search algorithm to a remote device.

\* \* \* \* \*